US008709022B2

(12) United States Patent
Stone et al.

(10) Patent No.: US 8,709,022 B2
(45) Date of Patent: Apr. 29, 2014

(54) METHOD AND APPARATUS FOR PASSING A SUTURE

(75) Inventors: Kevin T. Stone, Winona Lake, IN (US);
Chris Palese, South Whitley, IN (US);
Douglas M. Lorang, North Logan, UT (US); Andrew Fauth, River Heights, UT (US); Darin Ewer, Providence, UT (US); Ephraim Akyuz, Logan, UT (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 0 days.

(21) Appl. No.: 13/114,488

(22) Filed: May 24, 2011

(65) Prior Publication Data
US 2012/0303046 A1    Nov. 29, 2012

(51) Int. Cl.
*A61B 17/04*    (2006.01)
(52) U.S. Cl.
USPC ........................................ 606/144; 606/145
(58) Field of Classification Search
USPC .......................................... 606/139–145, 148
See application file for complete search history.

(56) References Cited

U.S. PATENT DOCUMENTS

| 4,187,210 | A | | 2/1980 | Howard, Jr. | |
|---|---|---|---|---|---|
| 5,037,928 | A | | 8/1991 | Li et al. | |
| 6,102,920 | A | * | 8/2000 | Sullivan et al. | 606/147 |
| 6,893,448 | B2 | | 5/2005 | O'Quinn et al. | |
| 7,118,583 | B2 | | 10/2006 | O'Quinn et al. | |
| 7,232,448 | B2 | | 6/2007 | Battles et al. | |
| 2003/0220658 | A1 | * | 11/2003 | Hatch et al. | 606/139 |
| 2005/0085831 | A1 | * | 4/2005 | Rioux | 606/144 |
| 2007/0038230 | A1 | * | 2/2007 | Stone et al. | 606/139 |
| 2008/0091219 | A1 | | 4/2008 | Marshall et al. | |
| 2009/0018554 | A1 | * | 1/2009 | Thorne et al. | 606/145 |
| 2010/0114123 | A1 | | 5/2010 | Nason | |
| 2011/0295279 | A1 | | 12/2011 | Stone et al. | |
| 2012/0303046 | A1 | | 11/2012 | Stone et al. | |

FOREIGN PATENT DOCUMENTS

WO    WO-9416645    8/1994

OTHER PUBLICATIONS

International Search Report mailed Apr. 15, 1994 for PCT/US94/01243 claiming benefit of U.S. Appl. No. 13/114,483, filed May 24, 2011.

* cited by examiner

*Primary Examiner* — Gregory Anderson
*Assistant Examiner* — Christina Lauer
(74) *Attorney, Agent, or Firm* — Harness, Dickey

(57) ABSTRACT

A suture passing instrument including an operation handle, a needle member, and a suture holder assembly. The operation handle has at least one actuator movable between a first position and a second position. The needle member extends from the operation handle. The needle member has a curved end portion and defines an eyelet extending therethrough. The suture holder assembly extends from the operation handle and has a movable suture carrier at a distal end configured to hold a suture. The movable suture carrier has a suture pusher telescopically and movably received in the movable suture carrier. The suture carrier is movable between a retracted position and an extended position. The suture pusher is movable beyond the suture carrier to carry the suture through the eyelet.

23 Claims, 17 Drawing Sheets

METHOD AND APPARATUS FOR PASSING A SUTURE

CROSS-REFERENCE TO RELATED APPLICATIONS

The present application is related to U.S. patent application Ser. No. 13/114,483 entitled "Method and Apparatus for Passing a Suture" filed concurrently herewith, the disclosure of which is incorporated by reference.

FIELD

The present disclosure relates generally to tissue fixation; and more particularly relates to a method and apparatus for passing a suture through tissue.

BACKGROUND

This section provides background information related to the present disclosure which is not necessarily prior art.

In an anatomy, such as a human anatomy, various surgical procedures are often performed to repair or replace various portions thereof. For example, soft tissues of the body may tear or separate from bones due to trauma, overuse, surgical intervention, or disease. These soft tissues can be repaired and/or reattached using sutures or other fastening devices (e.g., screws, staples, or various types of suture anchors).

One means to repair a soft tissue, such as a labral tear, is to thread a suture through a selected portion of the soft tissue. The suture is retrieved from within the surgical site and the free ends of the suture may then be tied together to form a knot. In minimally invasive procedures (e.g., arthroscopic or laparoscopic procedures), however, the surgical site is not readily accessible and the surgeon's ability to thread the suture through the tissue manually is limited. Furthermore, the requisite instruments for retrieving the suture intracorporeally may require an enlarged surgical site.

SUMMARY

This section provides a general summary of the disclosure, and is not a comprehensive disclosure of its full scope or all of its features.

In one form, the present disclosure provides a suture passing instrument including an operation handle, a needle member, and a suture holder assembly. The operation handle can have at least one actuator movable between a first position and a second position. The needle member can extend from the operation handle. The needle member can have a curved end portion and an eyelet extending therethrough. The suture holder assembly can extend from the operation handle and have a movable suture carrier at a distal end configured to hold a suture. The movable suture carrier can have a suture pusher telescopically and movably received in the movable suture carrier. The suture carrier can be movable between a retracted position and an extended position. The suture pusher is movable beyond the suture carrier to carry the suture through the eyelet.

In another form, the present disclosure provides a method for passing a suture through a tissue. The method can include loading a suture into a pair of channels in a cannulated suture carrier. The method can also include inserting a curved end portion of a needle member through the tissue. The curved end portion can have an eyelet extending therethrough. The method can also include moving the cannulated suture carrier from a first position to a second position while carrying the suture. The cannulated suture carrier can have a suture pusher telescopically received therein. The method can then include moving the suture pusher from the second position to a third position to push the suture outwardly from the pair of channels and carry the suture through the eyelet of the needle member. The needle member can then be removed from the tissue to pass the suture through the tissue.

In another form, the present disclosure provides yet another method for passing a suture through a tissue. The method can include removably securing the suture in a pair of channels in a suture carrier. The method can also include rotating a helical end portion of a needle through the tissue. The needle can have an eyelet extending through a distal end of the helical end portion. An actuator can then be moved from a retracted position to an extended position, thereby extending a suture pusher located within the cannulated suture carrier into the eyelet of the needle member. While extending the suture pusher, the suture can be captured with a hook member, pushed outwardly from the pair of channels and through the eyelet of the needle member, and captured within a pair of semi-circular openings within the eyelet. The method can then include returning the actuator from the extended position to the retracted position, causing the suture pusher to retract from the eyelet while maintaining the suture within the semi-circular openings of the eyelet. The needle member can then be withdrawn from the tissue by rotating the operation handle in reverse to pass the suture through the tissue.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
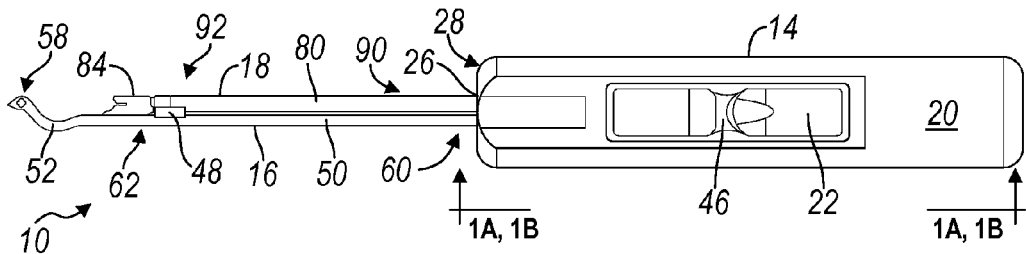
FIG. 1 is a top view of a right-helix suture passing instrument constructed in accordance with the teachings of the present disclosure.

The following description of various embodiments is merely exemplary in nature and is not intended to limit the present disclosure, its application, or uses. It should be understood that throughout the drawings, corresponding reference numerals indicate like or corresponding parts and features. With reference to FIGS. 1-14, various methods and apparatuses are disclosed according to the present teachings for passing a suture through an exemplary soft tissue, such as a labrum 121 (FIG. 4A) within a glenohumeral joint, T. However, the various apparatuses and methods may also be used for a plurality of procedures and to repair other soft tissues in the anatomy, such as those damaged through trauma, overuse, surgical intervention, or disease. Therefore, the various apparatuses and methods should not be limited to use only for tissue damage in the glenohumeral area. For example, the various instruments may be used to affix or hold a hamstring, Achilles tendon allograft, other soft tissue, or any other appropriate portion. In addition, although various embodiments may illustrate a suture knot for securing a selected tissue, it will be understood that any mode of securing the afflicted tissue may be used. Therefore, it will be understood that the following discussions are not intended to limit the scope of the present teachings or claims herein.

Referring now to FIGS. 1-4 of the drawings, a right-helix suture passing instrument is generally indicated by reference number 10. Suture passing instrument 10 may be operable for passing a suture 12 (FIG. 4) through the labrum 121 to assist in repairing the joint. Unless specifically mentioned, the various components of the suture passing instrument 10 are made of a biocompatible material, such as stainless steel, to allow for sterilization using chemicals or autoclaving. It is understood that select components described herein can be made from non-stainless steel materials and therefore those select components may not be suitable for all sterilization techniques due to heat sensitivity or chemical sensitivity of the materials. Moreover, suture passing instrument 10 may be a single-use (i.e., disposable) or may be a standardized instrument that can be fitted with removable and replaceable components.

Figure 1A:
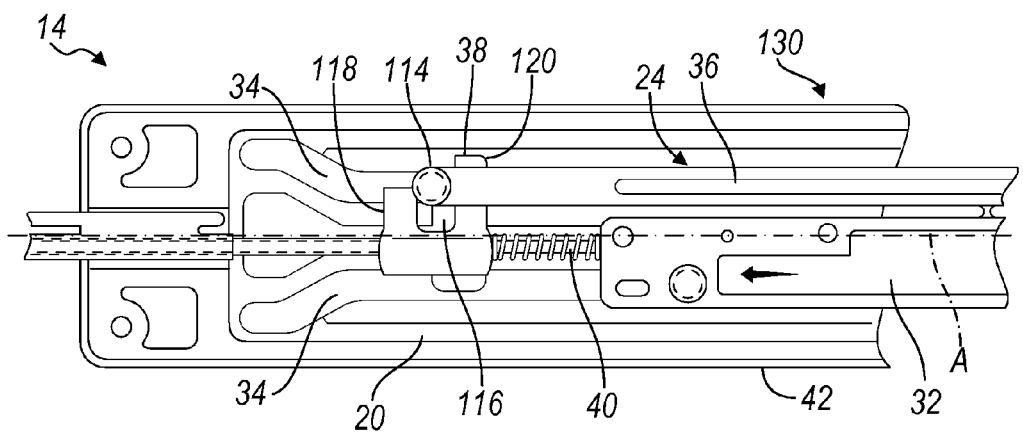
FIG. 1A is a sectional view of an operation handle for the suture passing instrument in a retracted position in accordance with the teachings of the present disclosure.
Figure 1B:
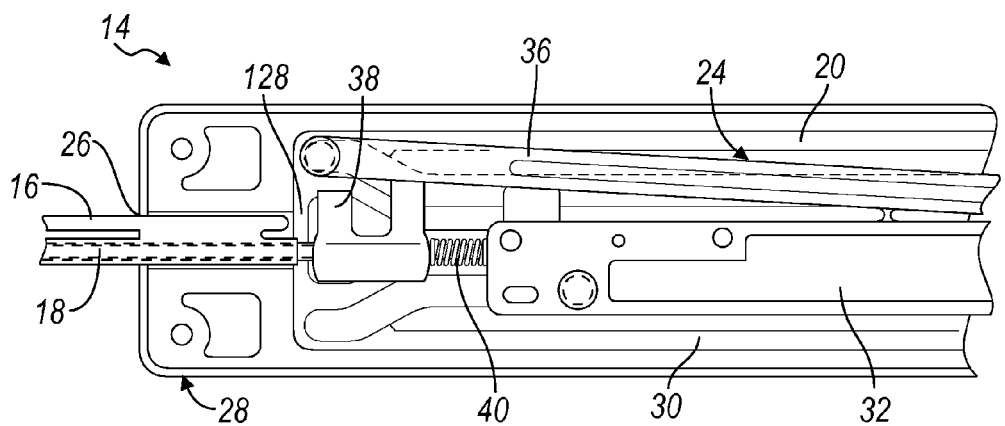
FIG. 1B is a sectional view of an operation handle for the suture passing instrument in an extended position in accordance with the teachings of the present disclosure.

With particular reference to FIGS. 1, 1A, and 1B, suture passing instrument 10 is shown to include an operation handle 14, an elongated shaft or needle member 16, and a suture holder assembly 18. The operation handle 14 further includes a handle body 20, an actuator 22 disposed thereon, and a slider mechanism 24 disposed therein. As shown and described, the handle body 20 may include at least one opening 26 at a distal end 28 for receiving the needle member 16 and the suture holder assembly 18, a central cavity 30 for receipt of a first slide member 32, and a plurality of curved channels 34 integrally formed in the handle body 20 for receipt of a second slide member 36. The slider mechanism 24 may include the pivotally attached first and second slide members 32, 36, a c-shaped translation member 38, and a spring 40. The first and second slide members 32, 36 may move longitudinally along the central cavity 30 and curved channels 34, respectively. Notably, the curved channels 34 may be mirrored about a center axis, A, of the operation handle 14 to allow for a single design for right- and left-handed handles. Furthermore, the handle body 20 may be formed from any biocompatible material (e.g., metal or polymer) and may also include a textured exterior surface 42 (e.g., knurl, padding) to provide comfort and/or grip for the operator.

Figure 4:
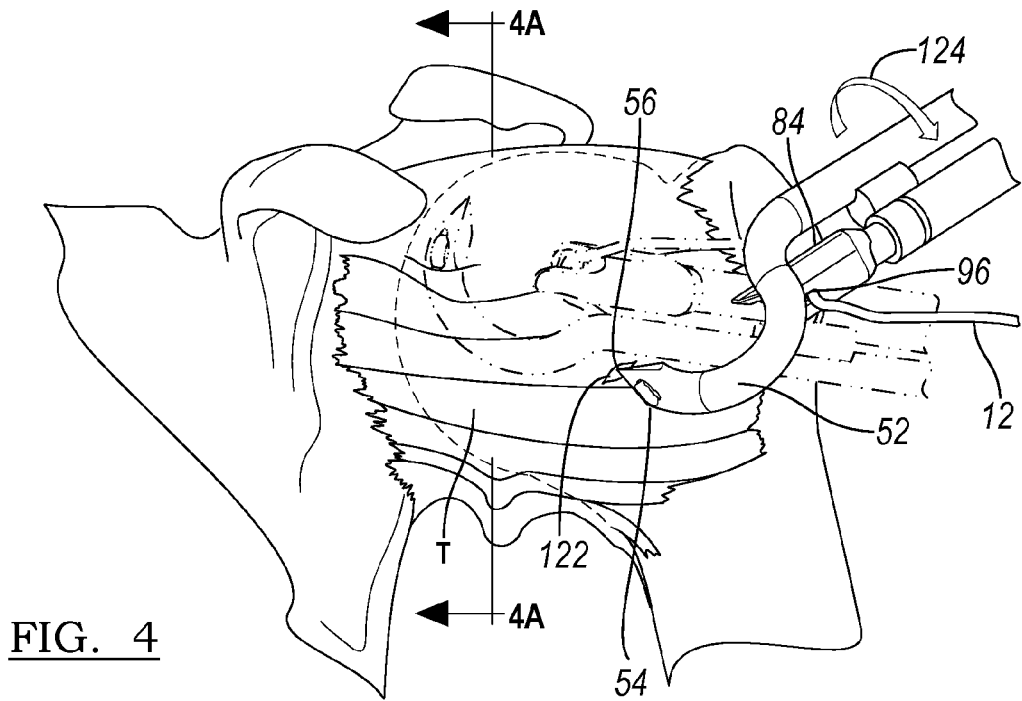
FIG. 4 is a perspective view of the suture passing instrument of FIG. 1 in an initial operative position in association with labrum tear within a glenohumeral joint.
Figure 4A:
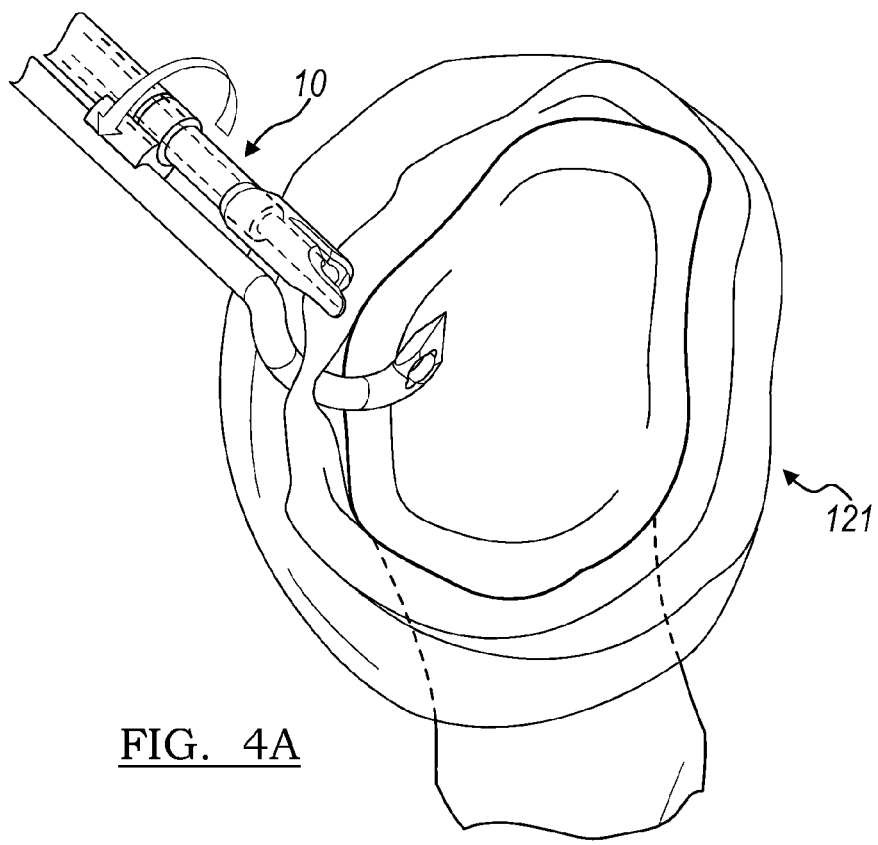
FIG. 4A is a cross-sectional view of the labrum tear of FIG. 4 taken through section 4A-4A.
Figure 4B:
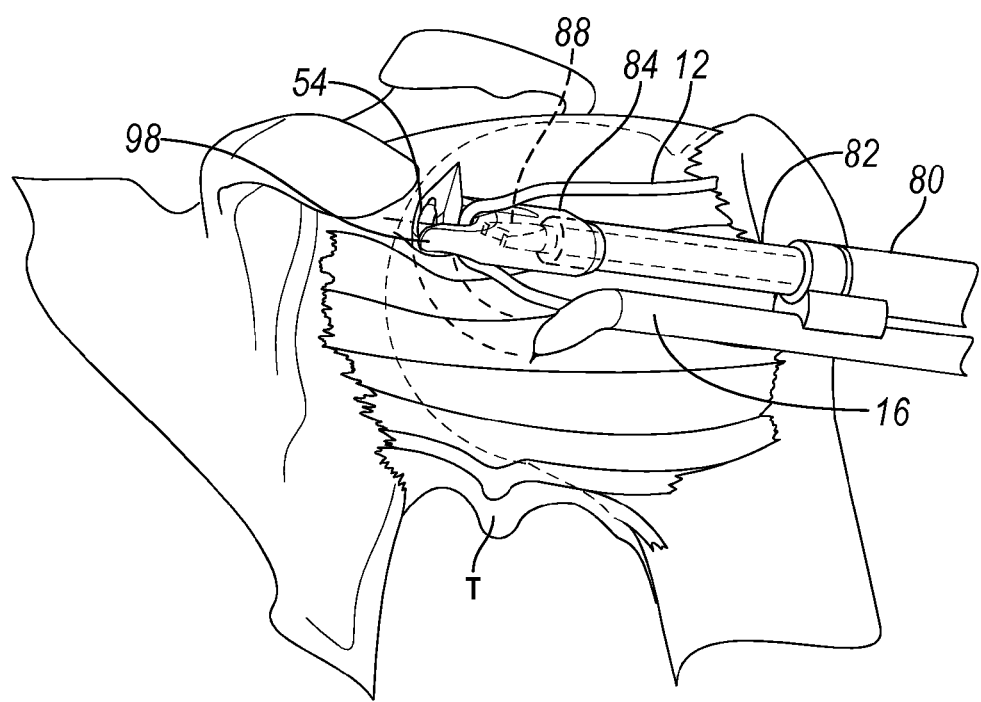
FIG. 4B is a perspective view of the suture passing instrument of FIG. 1 in an intermediate operative position depicting a suture holder advanced toward the needle tip.
Figure 4C:
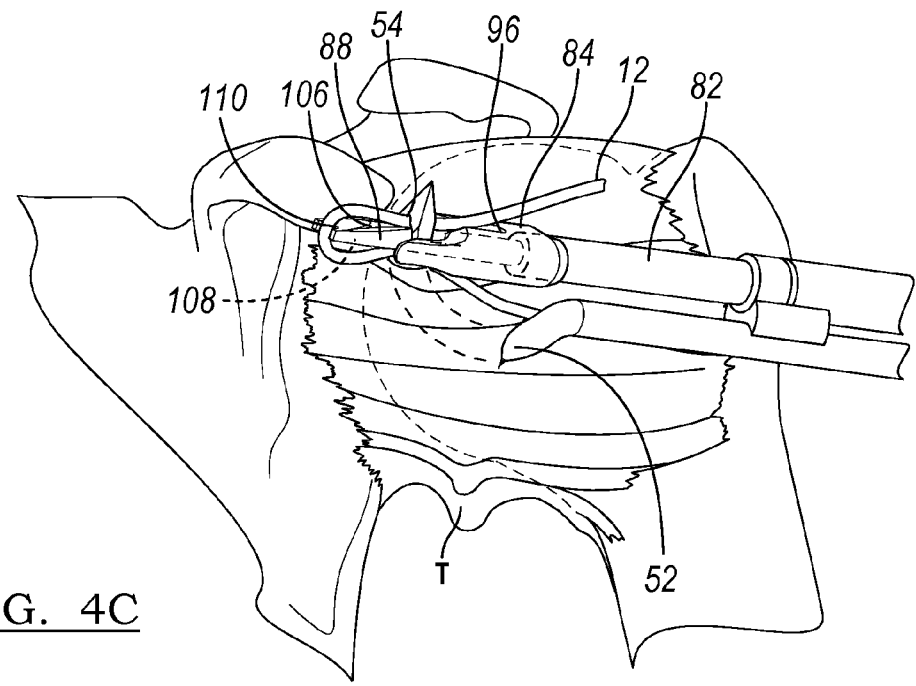
FIG. 4C is a perspective view of the suture passing instrument of FIG. 1 in an intermediate operative position depicting a suture pusher of the suture holder advancing a suture through the needle tip.

The actuator 22 may be a trigger member operable for actuating the slider mechanism 24 in a longitudinal direction along the handle body 20 from a first or retracted position (as shown in FIGS. 1 and 1A) to a second or extended position (as shown in FIGS. 4C and 1B). It is also contemplated that the actuator 22 may include multiple members 44 moving in tandem or moving independently (e.g., as shown in phantom in FIG. 6). The actuator 22 may define a centrally-raised, finger grip portion 46 for assisting an operator in movement between the retracted and extended positions. Although not shown, the actuator 22 may also incorporate the textured exterior surface (e.g., knurl, padding) to provide comfort and/or grip for the operator.

Figure 2:
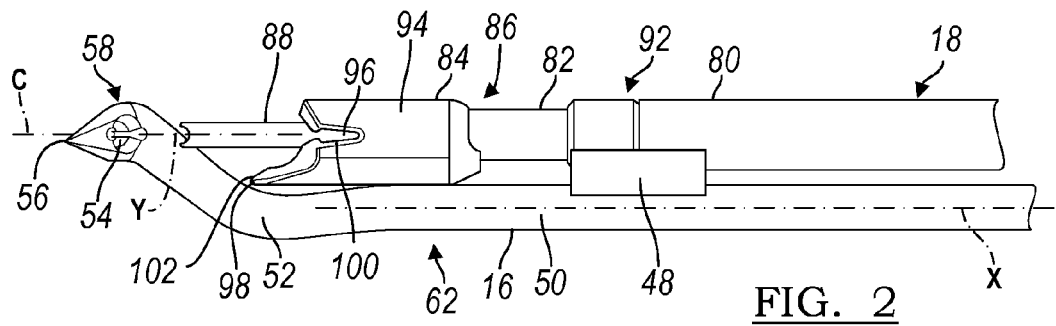
FIG. 2 is a side view of the suture passing instrument of FIG. 1.

With reference now to FIGS. 1 and 2, the needle member 16 and suture holder assembly 18 may extend from the distal end 28 of the handle body 20. Furthermore, the needle member 16 and suture holder assembly 18 may have a connection member 48 located therebetween. Both the needle member 16 and suture holder assembly 18 may be fixedly coupled to the operation handle 14 and the connection member 48 to maintain a parallel relationship and to prevent relative movement therebetween. It should be understood that the connection member 48 may be any device for securing the needle member 16 and the suture holder assembly 18 together, including but not limited to, an adhesive, a weld, and a fastener.

The needle member 16 may include a straight elongated shaft 50, a helical end 52 integrally formed with the elongated shaft 50, a needle eyelet 54 extending through the helical end 52, and a pointed tip 56 at a distal end 58 of the needle member 16. The elongated shaft 50 extends along a longitudinal axis, X, and has a first, proximal end 60 extending from the distal end 28 of the handle body 20 and a second, distal end 62 terminating a predetermined distance beyond the connection member 48. The helical end 52 may extend from the second end 62 of the elongated shaft 50 and may exhibit a "pig-tail" shape or right helix curve over its length. The right helix curve may follow the path of a spiral or a straight line drawn on a plane when that plane is wrapped around a cylindrical surface, such as a right circular cylinder. Accordingly, the helical end 52 may be rotated to bring a centerline, C, of the needle eyelet 54 into a coaxial arrangement with a longitudinal axis, Y, of the suture holder assembly 18. As can be seen, the longitudinal axis, X, of the elongated shaft 50 and the longitudinal axis, Y, of the suture holder assembly 18 are generally parallel to one another along their lengths.

Figure 3A:
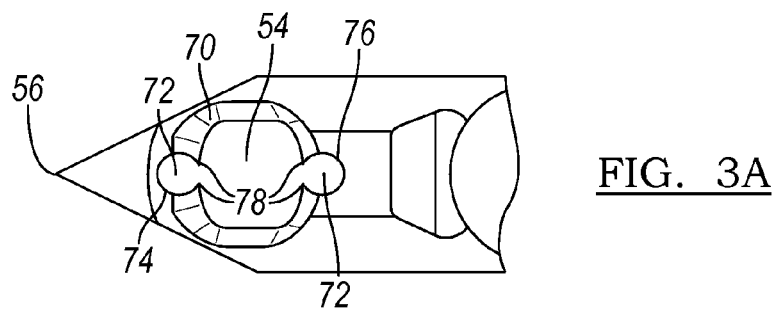
FIG. 3A is an enlarged view of a needle tip of the suture passing instrument of FIG. 2.

With particular reference to FIG. 3A, the needle eyelet 54 may define a generally hexagonal periphery 70 symmetrically arranged about a plane extending from the pointed tip 56 and through centerline, C. Furthermore, the needle eyelet 54 may define a pair of opposed semi-circular openings 72 arranged at and extending from distal and proximal ends 74, 76 of the hexagonal periphery 70. The semi-circular openings 72 may have pointed, opposed ends 78 terminating at the hexagonal periphery 70 for gripping the suture 12, as will be described in more detail below.

Referring again to FIGS. 1 and 2, suture holder assembly 18 may include a generally straight tubular shaft 80, a tubular extension rod 82 telescopically received within the tubular shaft 80, a cannulated suture carrier 84 at a distal end 86 of the tubular extension rod 82, and a suture pusher 88 telescopically arranged within the cannulated suture carrier 84. The generally tubular shaft 80 extends along the longitudinal axis, Y, and has a first, proximal end 90 extending from the distal end 28 of the handle body 20 and a second, distal end 92 terminating at the connection member 48. The tubular extension rod 82 is coupled to or in communication with both the actuator 22 and the cannulated suture carrier 84. Therefore, movement of actuator 22 causes movement of the tubular extension rod 82, as will be described in more detail below.

Figure 7:
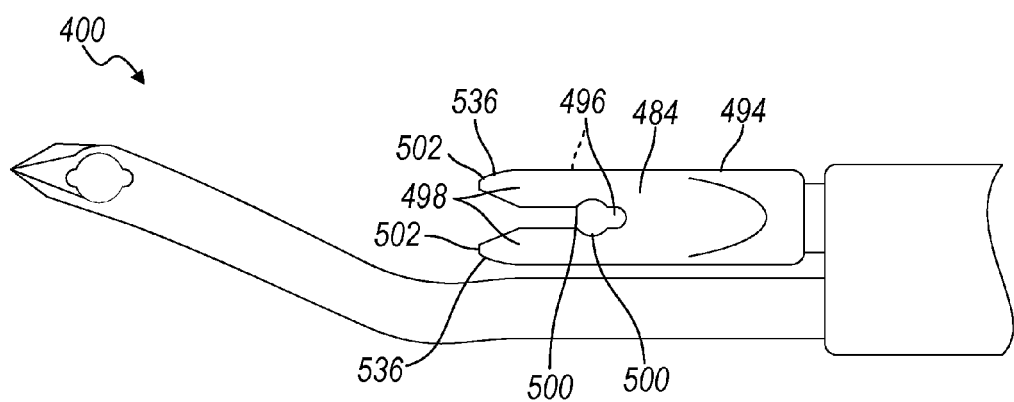
FIG. 7 is a perspective view of an alternate carrier body for the suture passing instrument of FIG. 1.

Cannulated suture carrier 84 may define a carrier body 94 having a pair of opposing, parallel channels 96, and an extended nose portion 98. The parallel channels 96 may have a predetermined length extending into the carrier body 94 and may have a width for receipt of sutures of various sizes. Accordingly, the parallel channels 96 may have sidewalls 100 that are angled (FIG. 2) or sidewalls 500 arranged in a decreasing step arrangement (FIG. 7). The nose portion 98 may extend outwardly from the carrier body 94 in a generally spade-shaped configuration, terminating at a nose tip 102. The nose tip 102 may be located adjacent to the needle member 16. The nose portion 98 may be angled to direct the suture 12 (FIG. 4A) into the parallel channels 96 of the carrier body 94 during loading of the suture 12.

Figure 3B:
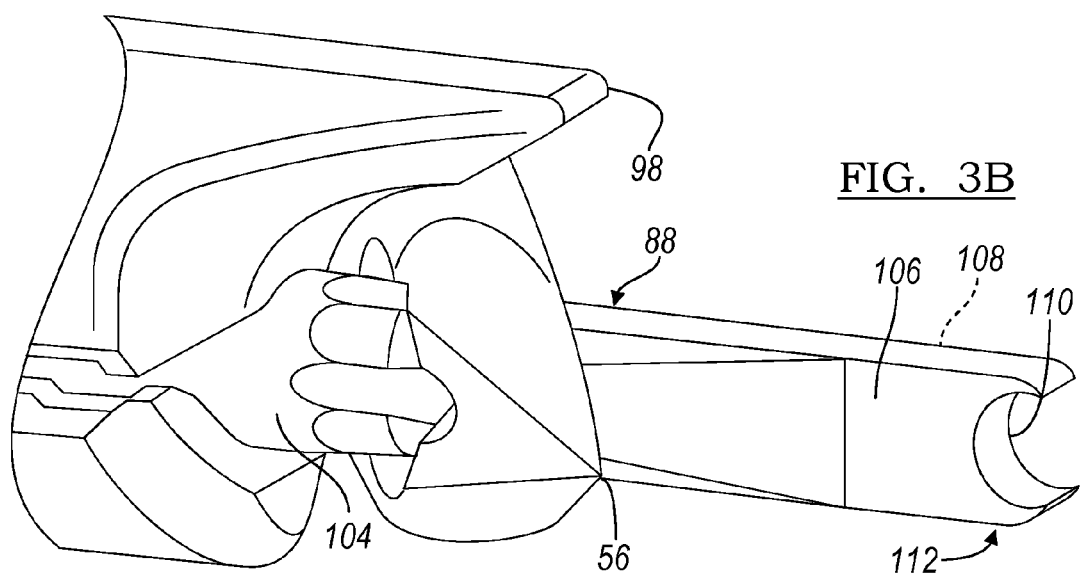
FIG. 3B is an enlarged view of a suture pusher of the suture passing instrument of FIG. 2.

With reference now to FIG. 3B, the suture pusher 88 may define a generally cylindrical pusher body 104, a pair of vertically-oriented, parallel surfaces 106, 108, and a channel or hook member 110 extending inwardly from a distal end 112 thereof. The suture pusher 88 may be sized to be movably received within the eyelet 54 of the needle member 16. Furthermore, the reduction in size from the generally cylindrical pusher body 104 to the integrally formed parallel surfaces 106, 108 allows for ingress of the suture 12 (FIG. 4A) within the eyelet 54 of the needle member 16. As shown, the hook member 110 may be a semi-circular indentation within the distal end 112 of the suture pusher 88. However, the hook member 110 may be any shape for retaining the suture 12 during movement of the suture pusher 88 towards the eyelet 54 of the needle member 16.

As can be seen from FIGS. 1 through 3, the suture pusher 88 may extend through the tubular extension rod 82 and the tubular shaft 80 for direct connection with the first slide member 32 in the operation handle 14. The spring 40 may extend over the suture pusher 88 in the operation handle 14 and abut the first slide member 32. The c-shaped translation member 38 may also extend over the suture pusher 88 in the operation handle 14 and may abut the other side of the spring 40 so as to contain the spring 40 between the c-shaped translation member 38 and the first slide member 32. The tubular extension rod 82 may be fixedly attached to the c-shaped translation member 38 opposite the spring 40.

The second slide member 36 may include an extending pin 114 drivingly contacting the c-shaped translation member 38. In the retracted position, the extending pin 114 may be located at a central portion 116 between a short leg 118 and a parallel long leg 120 of the c-shaped translation member 38. When the actuator 22 moves to the extended position, the second slide member 36 moves along the curved channel 34. The extending pin 114 contacts the short leg 118 causing it to move longitudinally, as well. As the second slide member 36 reaches the distal end 28 of the handle body 20, however, the extending pin 114 curves away from the short leg 118 along the channel 34, removing the longitudinal translation force from the c-shaped translation member 38.

Operation of the suture passing instrument 10 will now be described with reference to the labrum 121 of the glenohumeral joint, T, shown in FIGS. 4-4F and the slider mechanism 24 shown in FIGS. 1A and 1B. The labrum 121 is depicted in detail in FIG. 4A as it is within the glenohumeral joint, T, but it is obstructed from view in the other figures in order to shown positioning of the helix in the tissue. It should be understood that the repair as described herein is being completed on the labrum 121. Initially with the actuator 22 in the retracted position, the appropriately sized suture 12 is loaded into the parallel channels 96 of the cannulated suture carrier 84. The suture 12 may be loaded transversely to the longitudinal axis, Y, by dragging the suture 12 along the incline of the nose portion 98. The angle of the sidewalls 100 (FIG. 2) may allow the suture 12 to extend within the parallel channels 96 to be removably retained therewith.

With particular reference to FIGS. 4 and 4A, the pointed tip 56 of the helical end 52 is brought into contact with the labrum 121 of the glenohumeral joint, T, with no rotational movement. The sharpened point of the tip 56 pierces the ligament, T, and allows the suture passing instrument 10 to establish an opening 122 within the labrum 121 within the joint, T. As the suture passing instrument 10 is inserted through the opening 122, the operation handle 14 is rotated in a counter-clockwise manner, as shown by rotational arrow 124, in order to maintain a minimal size for the opening 122. The operation handle 14 may be rotated anywhere between approximately one-quarter of a turn to one full revolution to extend the needle eyelet 54 out of the ligament, T. The amount of rotation for the operation handle 14 may depend upon the dimensional shape of the curve of the helical end 52. The final orientation of the helical end 52 is shown in phantom.

Referring now to FIGS. 1A, 1B, and 4B, after the helical end 52 of the needle member 16 is fully and thoroughly inserted into the ligament, T, the actuator 22 is moved to the extended position. The actuator 22 is fixedly attached to the slider mechanism 24, so that longitudinal movement of the actuator 22 to the extended position, in turn, causes movement of the slider mechanism 24. In particular, the actuator 22 drives the slider mechanism 24 towards the distal end 28 of the handle body 20. This longitudinal movement causes the first and second slide members 32, 36 to translate in the central cavity 30 and curved channels 34, respectively. As previously described, the extending pin 114 of the second slide member 36 drivingly moves the short leg 118 of the c-shaped translation member 38. The concurrent movement of the first slide member 32 and the c-shaped translation member 38 cause the tubular extension rod 82 and the suture pusher 88 to extend through the tubular shaft 80 at an equivalent speed. Accordingly, the tubular extension rod 82 and suture pusher 88 of the suture holder assembly 18 move distally out of the tubular shaft 80 directing the cannulated suture carrier 84 towards the needle eyelet 54.

As the second slide member 36 reaches the distal end 28 of the handle body 20, the extending pin 114 curves away from the short leg 118 along the channel 34, removing its longitudinal driving force. The c-shaped translation member 38 may then contact a stop 128 located at the distal end 28 of the handle body 20, preventing any further longitudinal movement of the c-shaped translation member 38 and the tubular extension rod 82. This stopped motion of the c-shaped translation member 38 equates to a stopped motion of the cannulated suture carrier 84 when the nose portion 98 extends over the helical end 52 of the needle member 16 and the cannulated suture carrier 84 extends to a predetermined distance away from the needle member 16.

With reference now to FIGS. 1A, 1B, 3A, and 4C, the first slide member 32 continues its longitudinal translation through the central cavity 30, compressing the spring 40 as it moves. As should be understood, the suture pusher 88 continues movement with the first slide member 32, which causes its extension from the tubular extension rod 82 and the cannulated suture carrier 84. In this motion, the hook member 110 captures the suture 12 retained by the parallel channels 96 of the cannulated suture carrier 84 and pulls the suture 12 out of the channels 96. The hook member 110 and at least a portion of the parallel surfaces 106, 108 extend through the needle eyelet 54, forcing the suture 12 therethrough.

Once within the needle eyelet 54, the suture 12 may be eased towards the semi-circular openings 72 by the tapered shape of the suture pusher 88 and by arrangement of the angled shape of the hexagonal periphery 70. The opposed ends 78 of the semi-circular openings 72 may then receive the suture 12 for retention therewith. It should be understood that the opposed ends 78 might slightly flex as the suture 12 is eased towards the semi-circular openings 72. Furthermore, the opposed ends 78 may "bite" into fibers of the suture 12 to provide the requisite retention for the suture 12.

Figure 4D:
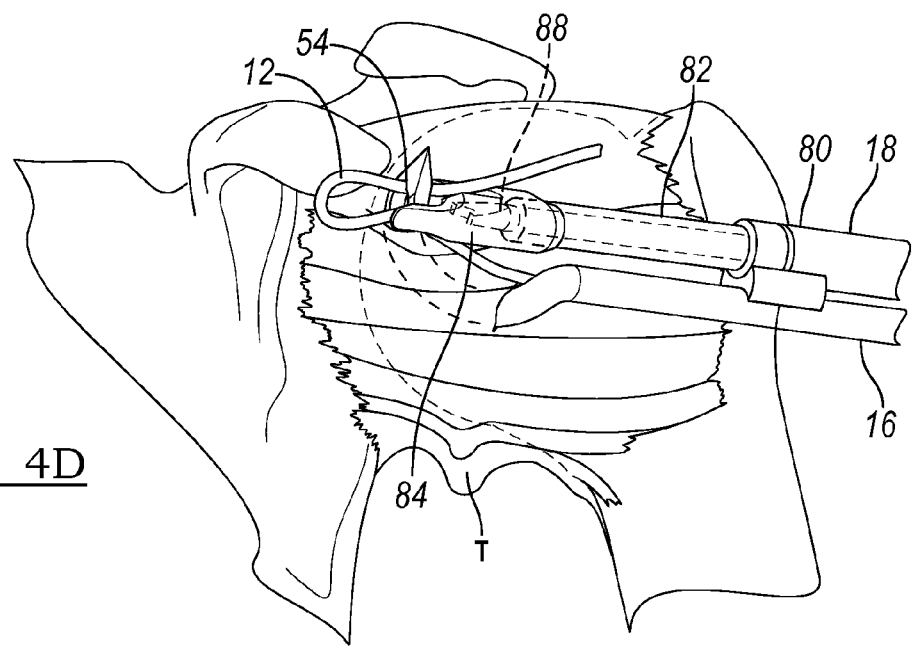
FIG. 4D is a perspective view of the suture passing instrument of FIG. 1 in an intermediate operative position depicting the pusher of the suture holder retracted from the needle tip.

Referring now to FIGS. 1A, 1B, and 4D, after the suture 12 extends through the needle eyelet 54 a predetermined distance, the operator may then return the actuator 22 to the retracted position. During retraction, the operator may remove the longitudinal force from the actuator 22 allowing the first slide member 32 to snap back from the distal end 28 of the handle body 20 due to force from the spring 40. The suture pusher 88, likewise, returns to its initial position within the cannulated suture carrier 84.

Figure 4E:
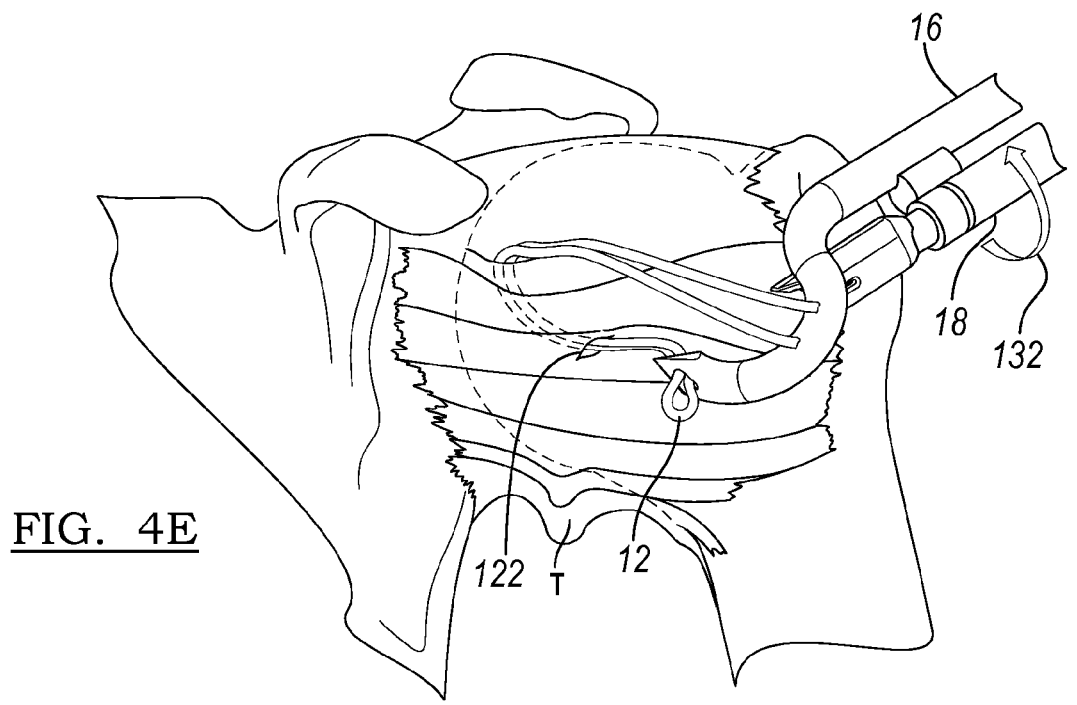
FIG. 4E is a perspective view of the suture passing instrument of FIG. 1 in a final retracted position and being removed from the glenohumeral tissue.

With reference now to FIGS. 1A, 1B, and 4E, the actuator 22 is returned to the retracted position by applying a reverse longitudinal force therewith. In particular, the actuator 22 drives the slider mechanism 24 towards a proximal end 130 of the handle body 20. This longitudinal movement causes the first and second slide members 32, 36 to translate in a reverse direction in the central cavity 30 and curved channels 34. As the second slide member 36 moves away from the distal end 28 of the handle body 20, the extending pin 114 curves back towards the c-shaped translation member 38 and drivingly engages the long leg 120 of the c-shaped translation member 38. The concurrent movement of the first slide member 32 and the c-shaped translation member 38 cause the tubular extension rod 82 and the suture pusher 88 to retract into the tubular shaft 80. Accordingly, the cannulated suture carrier 84 is withdrawn by the reverse movement of the tubular extension rod 82. Notably, however, the suture 12 is captured within the needle eyelet 54. The needle member 16 may then be withdrawn from the ligament, T, carrying the suture 12 therewith. Withdrawal of the needle member 16 is accomplished in reverse of insertion (i.e., rotation occurs in a clockwise motion), as shown by rotational arrow 132, with the needle member 16 being removed from the ligament, T, at the opening 122.

Figure 4F:
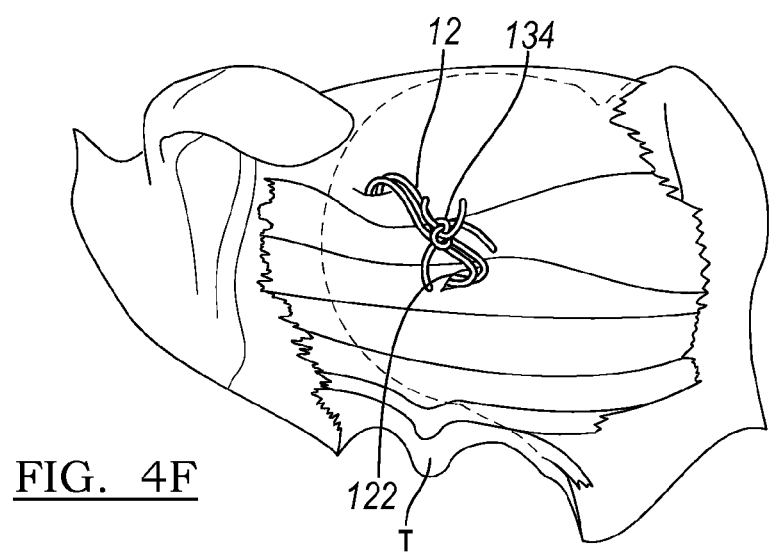
FIG. 4F is a perspective view of the glenohumeral tissue after removal of the suture passing instrument and securement of the suture.

Referring now to FIG. 4F, the suture 12 is then threaded through the opening 122 within the glenohumeral ligament, T. Ends of the suture 12 can then be knotted 134 outside of the surgical opening for a minimally invasive repair.

Figure 5:
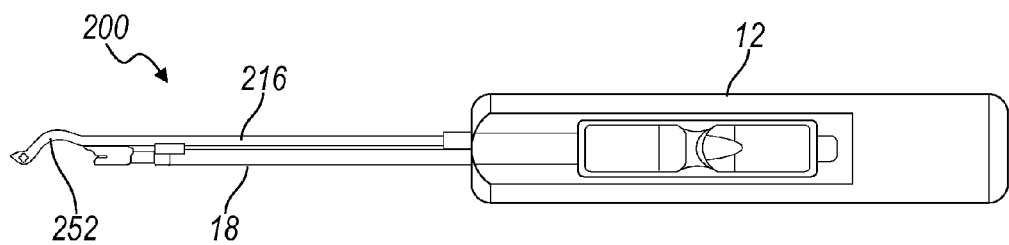
FIG. 5 is a perspective view of a left-helix suture passing instrument in association with a handle member.

With reference now to FIG. 5, an alternative suture passing instrument 200 is shown. Suture passing instrument 200 is also operable for passing the suture 12 through the labrum 121 to assist in repairing the joint, as previously described with respect to suture passing instrument 10. Furthermore, many of the components of suture passing instrument 10 remain unchanged in suture passing instrument 200. For example, suture passing instrument 200 uses a similar operation handle 14 and suture holder assembly 18. Suture passing instrument 200, however, exhibits a left helix curve at a helical end 252 of a needle member 216, instead of the right helix curve described with respect to the suture passing instrument 10. Accordingly, during insertion of the suture passing instrument 200, the operation handle 14 must be rotated in a clockwise manner in order to maintain the minimal size for the opening 122. While suture passing instrument 10 and suture passing instrument 200 are highly similar, certain surgeons may prefer one design to the other due to right- or left-hand dominance or for other reasons not articulated herein.

Figure 6:
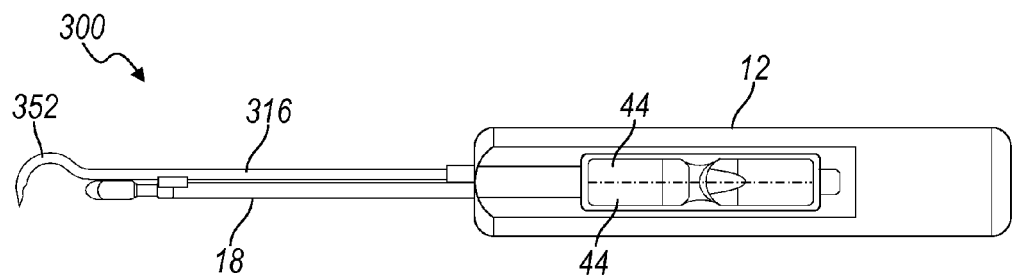
FIG. 6 is a perspective view of a linear curve suture passing instrument in association with a handle member.

Referring now to FIG. 6, another alternative suture passing instrument 300 is shown. Suture passing instrument 300 is also operable for passing the suture 12 through the labrum 121 to assist in repairing the joint, as previously described with respect to suture passing instrument 10. Furthermore, many of the components of suture passing instrument 10 remain unchanged in suture passing instrument 300. For example, suture passing instrument 300 uses a similar operation handle 14 and suture holder assembly 18. Suture passing instrument 300, however, exhibits a linear curve (i.e., "ice cream scoop") at an end 352 of a needle member 316, instead of the right helix curve at the helical end 52 described with respect to the suture passing instrument 10. Accordingly, during insertion of the suture passing instrument 300, the operation handle 14 need only to be moved in a single plane in order to maintain the minimal size for the opening 122. While suture passing instrument 10 and suture passing instrument 300 are highly similar, certain surgeons may prefer one design to the other due to space considerations or for other reasons not articulated herein.

Referring now to FIG. 7, another alternative suture passing instrument 400 is shown having an alternate cannulated suture carrier 484 associated with the tubular extension rod 82. Cannulated suture carrier 484 is operable for receiving the suture 12 and directing it towards the needle eyelet 54, as described with respect to cannulated suture carrier 84. Furthermore, many of the components of cannulated suture carrier 84 remain unchanged in cannulated suture carrier 484. Cannulated suture carrier 484, however, includes a pair of extending nose portions 498 mirrored about a pair of opposing, parallel channels 496. The parallel channels 496 may have a predetermined length extending into a carrier body 494 of the cannulated suture carrier 484. Accordingly, the parallel channels 496 may have sidewalls 500 that are angled for receipt of the suture 12.

The extending nose portions 498 may extend outwardly from the carrier body 494 in a generally spade-shaped configuration, terminating at a pair of nose tips 502. The nose portions 498 may be interiorly angled towards the parallel channels 496, so as to direct the suture 12 into the parallel channels 496 of the carrier body 494 during suture 12 loading. The nose tips 502 may also exhibit an exterior curve 536 with the carrier body 494 in order to gently push tissue away from the needle eyelet 54 during operation.

Figure 8:
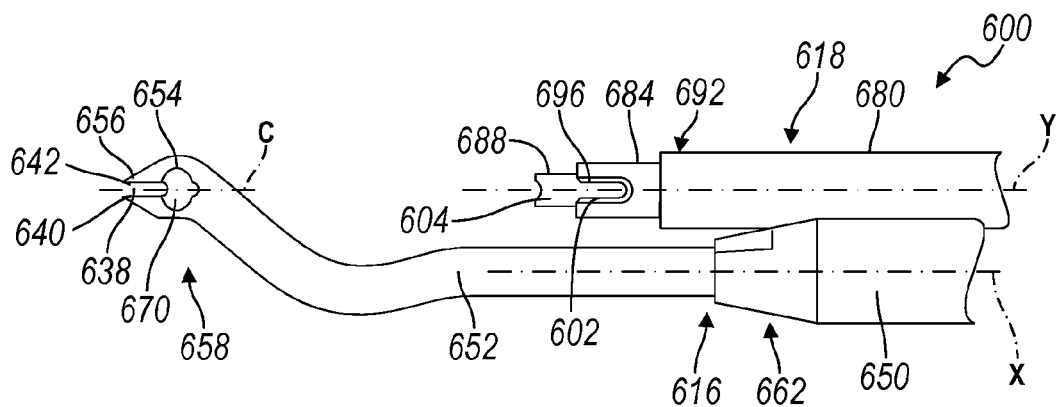
FIG. 8 is a perspective view of an alternate suture passing instrument constructed in accordance with the teachings of the present disclosure.

With reference now to FIG. 8, yet another alternative suture passing instrument 600 is shown. Suture passing instrument 600 is also operable for passing a suture through the labrum 121 of the glenohumeral joint, T, to assist in repairing the tissue, as previously described with respect to suture passing instrument 10. Furthermore, suture passing instrument 600 uses a similar operation handle 14 and connection member 48, which are not shown and will not be described in detail herein. However, suture passing instrument 600 includes both an alternately designed needle member 616 and suture holder assembly 618 extending from the distal end 28 of the operation handle 14. Both the needle member 616 and the suture holder assembly 618 may be fixedly coupled to the operation handle 14 and the connection member 48 to maintain a parallel relationship and to prevent relative movement therebetween.

The needle member 616 may include an elongated shaft 650, a helical end 652 secured to the elongated shaft 650, a needle eyelet 654 extending through the helical end 652, and a pointed tip 656 at a distal end 658 of the helical end 652. While this embodiment depicts the helical end 652 removable from the elongated shaft 650, it should be understood that the elongated shaft 650 and helical end 652 might also be integrally formed as shown in the aforementioned embodiments. While certain embodiments herein discuss either a removable or integrally formed needle member, it should be understood that each embodiment of the suture passing instrument may incorporate either of the removable or integrally formed needle member. The removable needle member may be connected to the elongated shaft through any known means, such as, bayonet slot, threading, or interference fit. Furthermore, the removable needle member may be selected from a plurality of needle members or from a pre-packaged kit.

The elongated shaft 650 may extend along a longitudinal axis, X, a predetermined distance from the operation handle 14. The helical end 652 may extend from a distal end 662 of the elongated shaft 650 and may exhibit a "pig-tail" shape or helix curve over its length. The helix curve may be rotated either in a right- or left-handed direction to bring a centerline, C, of the needle eyelet 654 into a coaxial arrangement with a longitudinal axis, Y, of the suture holder assembly 618.

The needle eyelet 654 may define a generally circular profile 670 having an opening 638. The opening 638 may define a pair of opposing faces 640, 642 extending from the circular profile 670 and through the pointed tip 656. In a relaxed state, the needle eyelet 654 may have a first diameter as shown. The needle eyelet 654 may be expandable to a second diameter for receipt of the suture 12, wherein the opposing faces 640, 642 are biased apart, as will be described in more detail below.

Suture holder assembly 618 may include a generally tubular shaft 680, a cannulated suture carrier 684 telescopically received within the tubular shaft 680, and a suture pusher 688 telescopically received within the cannulated suture carrier 684. The generally tubular shaft 680 extends along the longitudinal axis, Y, and has a distal end 692 terminating near the distal end 662 of the elongated shaft 650 of the needle member 616. Cannulated suture carrier 684 may define a pair of opposing, parallel channels 696 having a predetermined length extending into the cannulated suture carrier 684 and may have a width for receipt of sutures of various sizes. Accordingly, the parallel channels 696 may have sidewalls 602 that are angled or arranged in a decreasing step arrangement. The suture pusher 688 may define a generally cylindrical pusher body 604 sized to be received within the eyelet 654 of the needle member 616. While suture passing instrument 600 is shown to include suture holder assembly 618, it is also contemplated that the suture holder assembly 18 may be used with this embodiment. As should be understood, each embodiment may interchange the suture holder assembly 18 and the suture holder assembly 618.

Operation of the suture passing instrument 600 will now be described with reference to the glenohumeral ligament, T, shown in FIGS. 9A-9E and the slider mechanism 24 shown in FIGS. 1A and 1B. Initially with the actuator 22 in the retracted position, the appropriately sized suture 12 is loaded into the parallel channels 696 of the cannulated suture carrier 684 transversely to the longitudinal axis, Y.

Figure 9A:
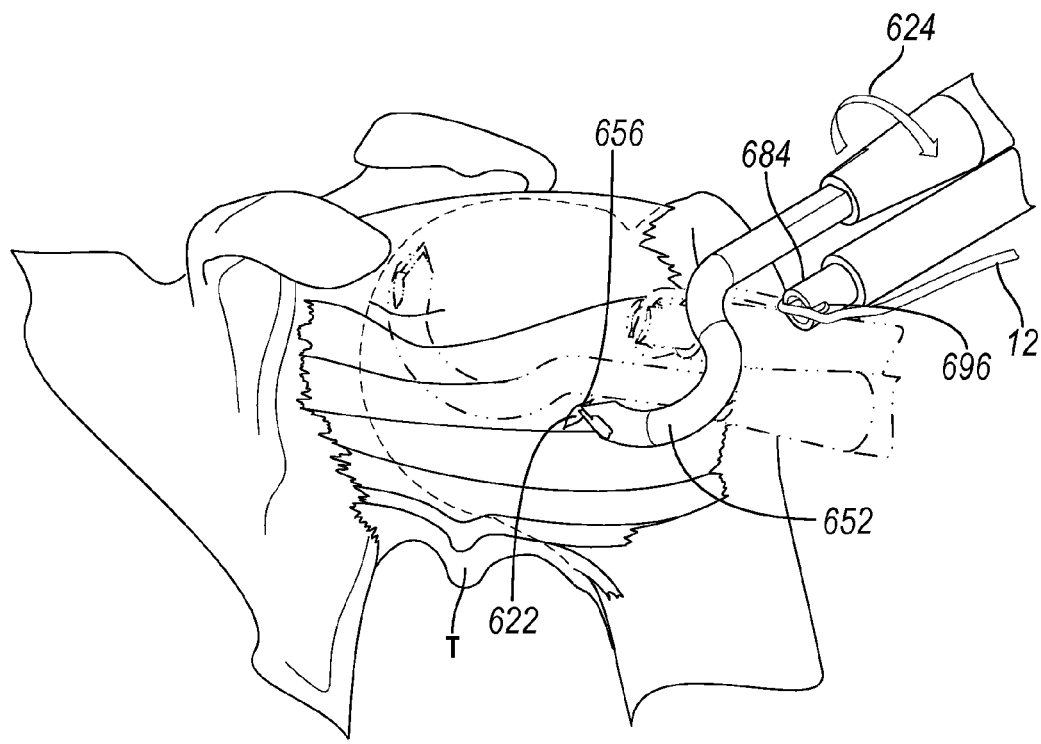
FIG. 9A is a perspective view of the suture passing instrument of FIG. 8 in an initial operative position in association with a glenohumeral tissue.

With particular reference to FIG. 9A, the pointed tip 656 of the helical end 652 is brought into contact with the labrum 121 (FIG. 4A) of the glenohumeral joint, T, with no rotational movement. The sharpened point of the tip 656 pierces the ligament, T, and allows the suture passing instrument 600 to establish an opening 622 within the ligament, T. As the suture passing instrument 600 is inserted through the opening 622, the operation handle 14 is rotated in a counter-clockwise manner, as shown by rotational arrow 624, in order to maintain a minimal size for the opening 622, as previously described. The operation handle 14 may be rotated anywhere between approximately one-quarter of a turn to one full revolution to extend the needle eyelet 654 out of the ligament, T. The amount of rotation for the operation handle 14 may depend upon the dimensional shape of the curve of the helical end 652. The final orientation of the helical end 652 is shown in phantom.

Figure 9B:
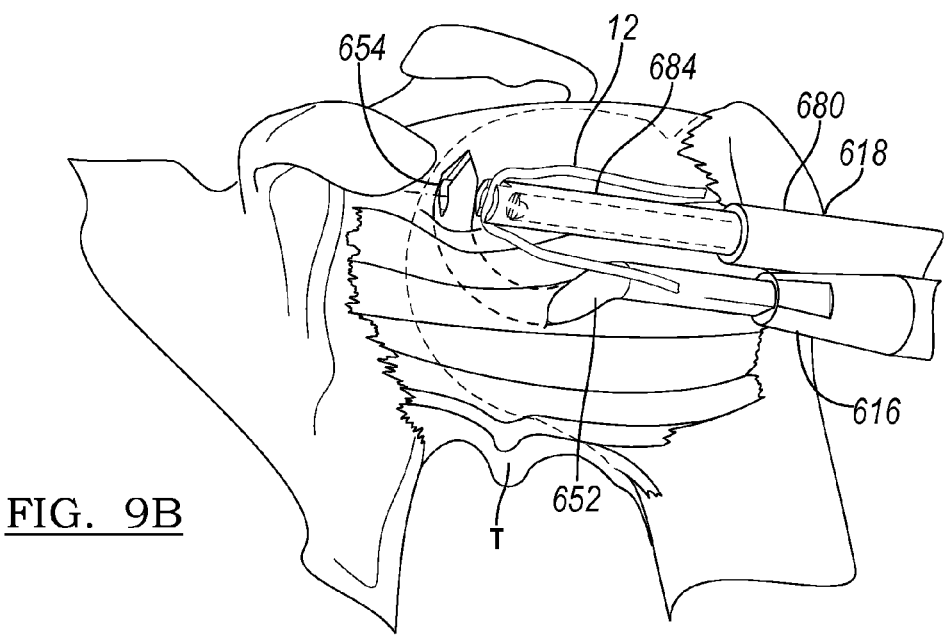
FIG. 9B is a perspective view of the suture passing instrument of FIG. 8 in an intermediate operative position depicting a suture holder advanced toward a needle tip.
Figure 9C:
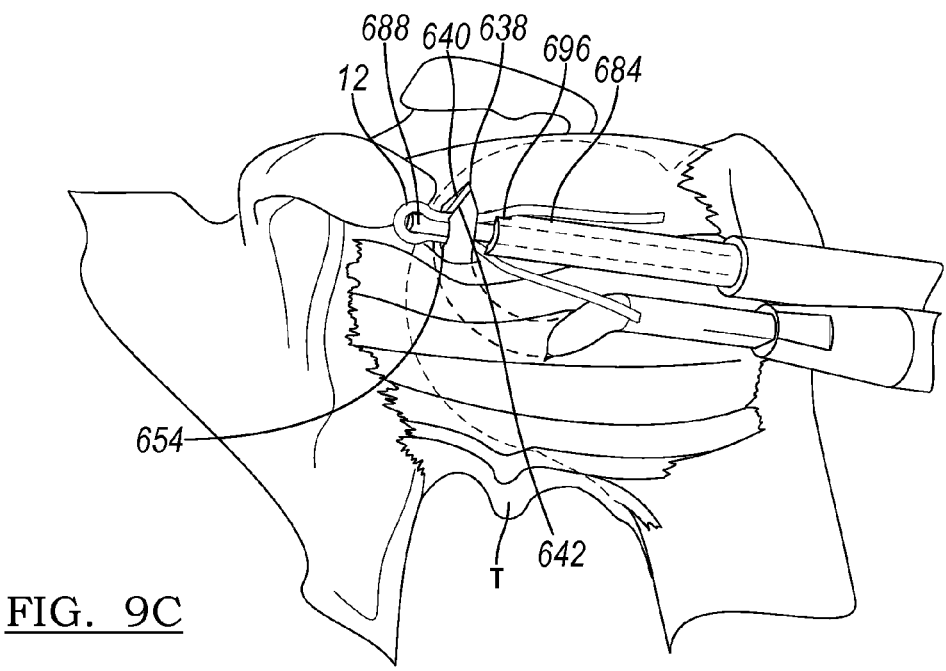
FIG. 9C is a perspective view of the suture passing instrument of FIG. 8 in an intermediate operative position depicting a pusher of the suture holder advanced through the needle tip.

Referring now to FIGS. 1A, 1B, and 9B, after the helical end 652 of the needle member 616 is fully and thoroughly inserted into the ligament, T, the actuator 22 is moved to the extended position. As previously described, the actuator 22 is fixedly attached to the slider mechanism 24, so that longitudinal movement of the actuator 22 to the extended position, in turn, causes movement of the slider mechanism 24. In particular, the actuator 22 drives the slider mechanism 24 towards the distal end 28 of the handle body 20. This longitudinal movement causes the first and second slide members 32, 36 to translate in the central cavity 30 and curved channels 34, respectively. The extending pin 114 of the second slide member 36 drivingly moves the short leg 118 of the c-shaped translation member 38. The concurrent movement of the first slide member 32 and the c-shaped translation member 38 cause the cannulated suture carrier 684 and the suture pusher 688 to extend through the tubular shaft 680 at an equivalent speed. Accordingly, the cannulated suture carrier 684 of the suture holder assembly 618 moves distally outwardly from the tubular shaft 680 directing the suture 12 towards the needle eyelet 654.

As the second slide member 36 reaches the distal end 28 of the handle body 20, the extending pin 114 curves away from the short leg 118, removing its longitudinal driving force. The c-shaped translation member 38 may then contact the stop 128 located at the distal end 28 of the handle body 20, preventing any further longitudinal movement of the c-shaped translation member 38 and the cannulated suture carrier 684. This stopped motion of the c-shaped translation member 38 equates to a stopped motion of the cannulated suture carrier 684 a predetermined distance from the eyelet 654 of the needle member 616.

With reference now to FIGS. 1A, 1B, 8, and 9C, the first slide member 32 continues its longitudinal translation through the central cavity 30, compressing the spring 40 as it moves. As should be understood, the suture pusher 688 continues movement with the first slide member 32, which causes its extension from the cannulated suture carrier 684. In this motion, the suture pusher 688 forces the suture 12 out of the channels 696. At least a portion of the suture pusher 688 extends through the needle eyelet 654, expanding the needle eyelet 654 at the opening 638. This expansion biases the opposing faces 640, 642 of the opening 638 apart and flexes the needle eyelet 654 to the enlarged, second diameter. The suture 12 can then be pushed into the eyelet 654.

Figure 9D:
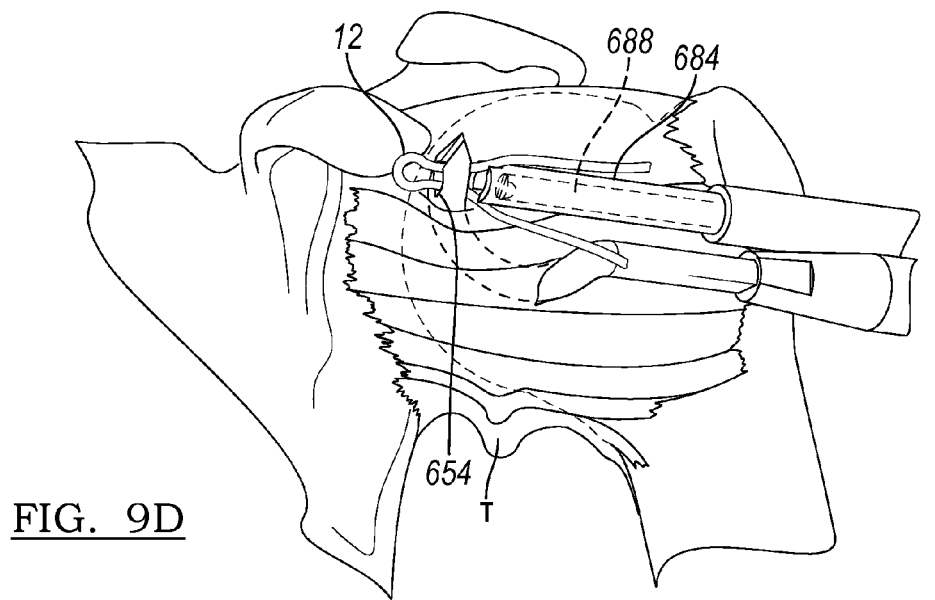
FIG. 9D is a perspective view of the suture passing instrument of FIG. 8 in an intermediate operative position depicting the pusher of the suture holder retracted from the needle tip.

Referring now to FIGS. 1A, 1B, and 9D, after the suture 12 extends through the needle eyelet 654 a predetermined distance, the operator may then return the actuator 22 to the retracted position. During retraction, the operator may remove the longitudinal force from the actuator 22 allowing the first slide member 32 to snap back from the distal end 28 of the handle body 20 due to force from the spring 40. The suture pusher 688, likewise, returns to its initial position within the cannulated suture carrier 684. Notably, after removing the suture pusher 688 from the needle eyelet 654, the needle eyelet 654 returns to the first diameter contracted around the suture 12.

Figure 9E:
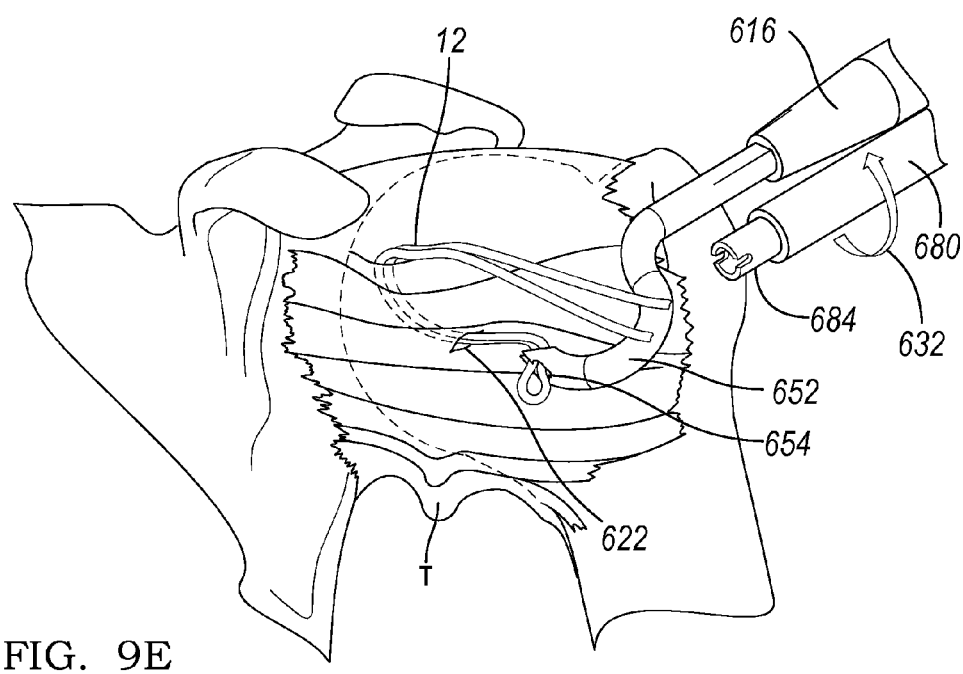
FIG. 9E is a perspective view of the suture passing instrument of FIG. 8 in a final retracted position and being removed from the glenohumeral tissue.

With reference now to FIGS. 1A, 1B, and 9E, the actuator 22 is returned to the retracted position by applying a reverse longitudinal force therewith. In particular, the actuator 22 drives the slider mechanism 24 towards the proximal end 130 of the handle body 20. This longitudinal movement causes the first and second slide members 32, 36 to translate in a reverse direction in the central cavity 30 and curved channels 34. As the second slide member 36 moves away from the distal end 28 of the handle body 20, the extending pin 114 curves back towards the c-shaped translation member 38 and drivingly engages the long leg 120 of the c-shaped translation member 38. The concurrent movement of the first slide member 32 and the c-shaped translation member 38 cause the cannulated suture carrier 684 and the suture pusher 688 to retract into the tubular shaft 680. Notably, however, the suture 12 remains captured within the needle eyelet 654. The needle member 616 may then be withdrawn from the ligament, T, carrying the suture 12 therewith. Withdrawal of the needle member 616 is accomplished in reverse of insertion (i.e., rotation occurs in a clockwise motion), as shown by rotational arrow 632, with the needle member 616 being removed from the ligament, T, at the tissue opening 622. Ends of the suture 12 can then be knotted 134 outside of the surgical site, as previously shown in FIG. 4F.

Figure 10:
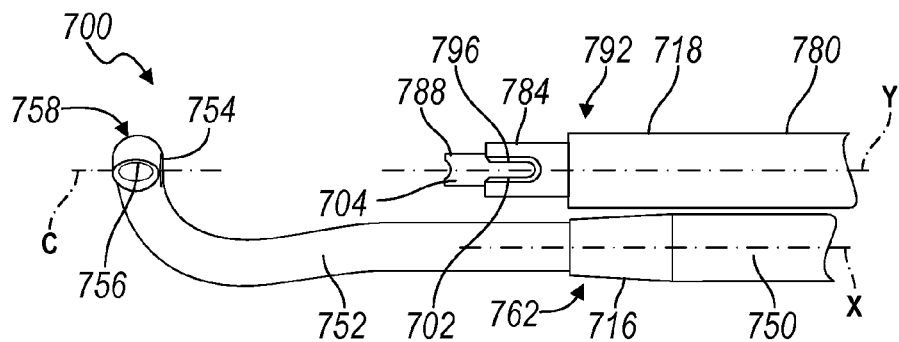
FIG. 10 is a perspective view of an alternate suture passing instrument constructed in accordance with the teachings of the present disclosure.

With reference now to FIG. 10, another alternative suture passing instrument 700 is shown. Suture passing instrument 700 is also operable for passing a suture through the labrum 121 of the glenohumeral joint, T, to assist in repairing the tissue, as previously described with respect to suture passing instrument 10. Furthermore, suture passing instrument 700 uses a similar operation handle 14 and connection member 48, which are not shown and will not be described in detail herein. However, suture passing instrument 700 includes both an alternately designed cannulated needle member 716 and suture holder assembly 718 extending from the distal end 28 of the operation handle 14. Both the cannulated needle member 716 and suture holder assembly 718 may be fixedly coupled to the operation handle 14 and the connection member 48 to maintain a parallel relationship and to prevent relative movement therebetween.

Figure 11A:
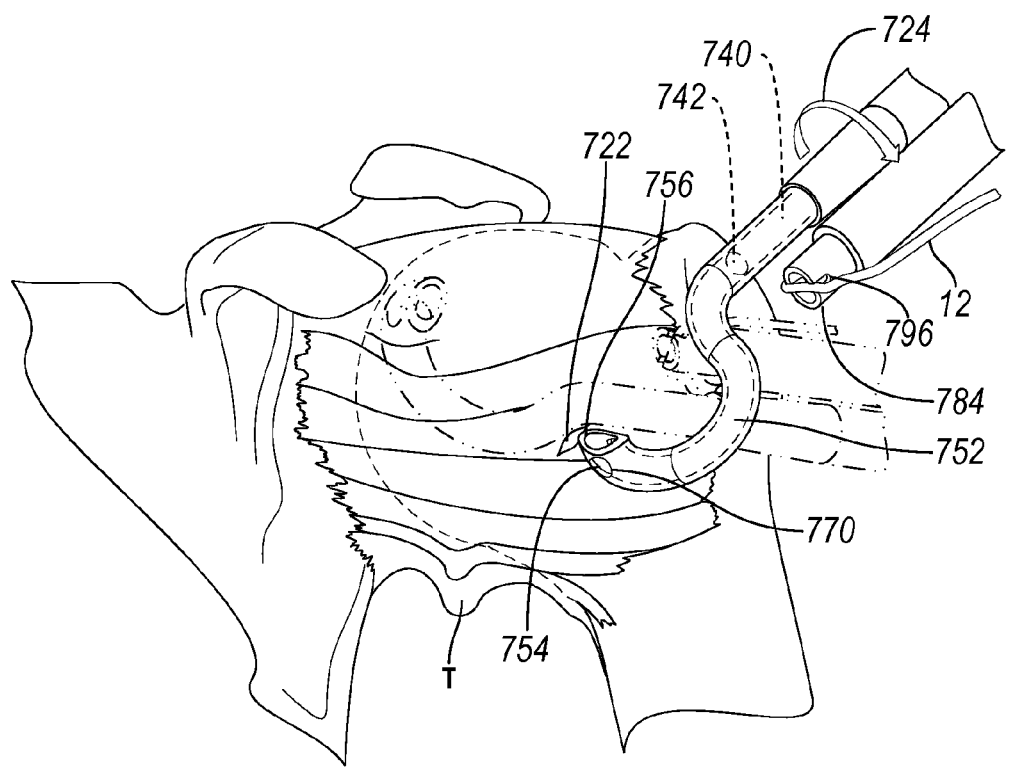
FIG. 11A is a perspective view of the suture passing instrument of FIG. 10 in an initial operative position in association with a glenohumeral tissue.

The cannulated needle member 716 may include an elongated shaft 750, a tubular helical end 752 secured to the elongated shaft 750, a generally circular needle eyelet 754 (best shown in FIG. 11A) extending through the helical end 752, a pointed tip 756 at a distal end 758 of the helical end 752, and a lock rod 740 movable within the elongated shaft 750 (FIG. 11A). While this embodiment depicts the helical end 752 separable from the elongated shaft 750, it should be understood that the elongated shaft 750 and helical end 752 may also be integrally formed as shown in the aforementioned embodiments.

The elongated shaft 750 may extend along a longitudinal axis, X, a predetermined distance from the operation handle 14. The helical end 752 may extend from a distal end 762 of the elongated shaft 750 and may exhibit a "pig-tail" shape or helix curve over its length. The helix curve may be rotated either in a right- or left-handed direction to bring a centerline, C, of the needle eyelet 754 into a coaxial arrangement with a longitudinal axis, Y, of the suture holder assembly 718.

The needle eyelet 754 may define a generally circular profile 770 extending through opposite sides of the tubular surface of the cannulated needle member 716. Furthermore, the lock rod 740 may be movable from a first, retracted position within the elongated shaft 750 to a second, extended position in the helical end 752. In the extended position, the lock rod 740 may extend transversely between the opposite sides of the tubular surface at the needle eyelet 754. Accordingly, a blunt end 742 of the lock rod 740 may terminate distal the needle eyelet 754. The lock rod 740 may be formed from a flexible material (e.g., nitinol) which can bend through the cannulated needle member 716.

Suture holder assembly 718 may include a generally tubular shaft 780, a cannulated suture carrier 784 telescopically received within the tubular shaft 780, and a suture pusher 788 telescopically received within the cannulated suture carrier 784. The generally tubular shaft 780 extends along the longitudinal axis, Y, and has a distal end 792 terminating near the distal end 762 of the elongated shaft 750 of the needle member 716. Cannulated suture carrier 784 may define a pair of opposing, parallel channels 796 having a predetermined length extending into the cannulated suture carrier 784 and may have a width for receipt of sutures of various sizes. Accordingly, the parallel channels 796 may have sidewalls 702 that are angled or arranged in a decreasing step arrangement. The suture pusher 788 may define a generally cylindrical pusher body 704 sized to be received within the eyelet 754 of the needle member 716. While suture passing instrument 700 is shown to include suture holder assembly 718, it is also contemplated that the suture holder assembly 18 may be used with this embodiment. As should be understood, each embodiment may interchange the suture holder assembly 18 and the suture holder assembly 718.

Operation of the suture passing instrument 700 will now be described with reference to the glenohumeral ligament, T, shown in FIGS. 11A-11E and the slider mechanism 24 shown in FIGS. 1A and 1B. Initially with the actuator 22 in the retracted position, the appropriately sized suture 12 is loaded into the parallel channels 796 of the cannulated suture carrier 784 transversely to the longitudinal axis, Y.

With particular reference to FIG. 11A, the pointed tip 756 of the helical end 752 is brought into contact with the labrum 121 (FIG. 4A) of the glenohumeral joint, T, with no rotational movement. The sharpened point of the tip 756 pierces the ligament, T, and allows the suture passing instrument 700 to establish an opening 722 within the ligament, T. As the suture passing instrument 700 is inserted through the opening 722, the operation handle 14 is rotated in a counter-clockwise manner, as shown by rotational arrow 724, in order to maintain a minimal size for the opening 722, as previously described. The operation handle 14 may be rotated anywhere between approximately one-quarter of a turn to one full revolution to extend the needle eyelet 754 out of the ligament, T. The amount of rotation for the operation handle 14 may depend upon the dimensional shape of the curve of the helical end 752. The final orientation of the helical end 752 is shown in phantom.

Figure 11B:
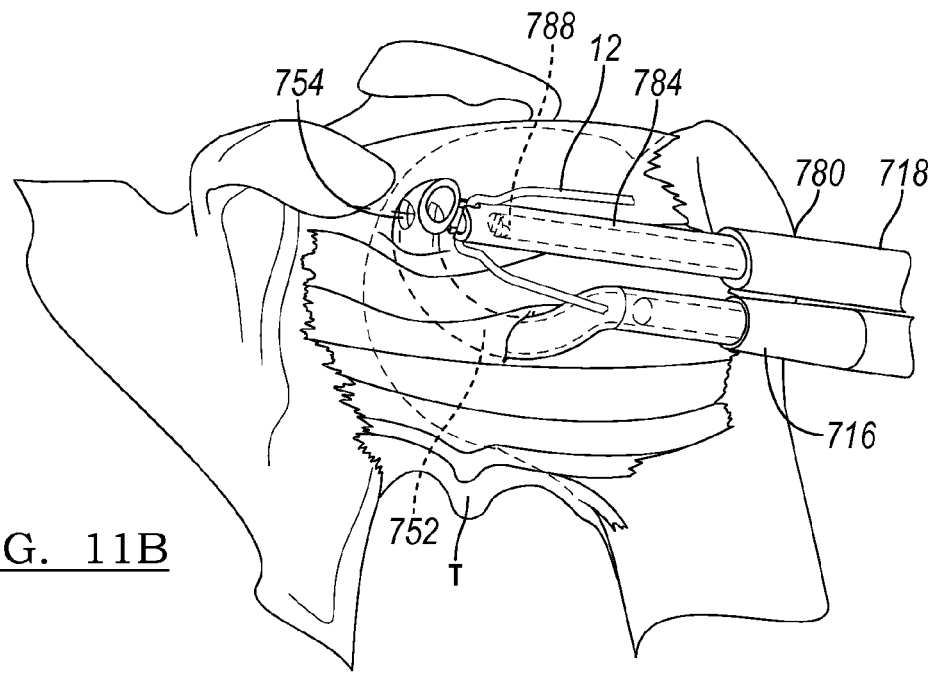
FIG. 11B is a perspective view of the suture passing instrument of FIG. 10 in an intermediate operative position depicting a suture holder advanced toward a needle tip.
Figure 11C:
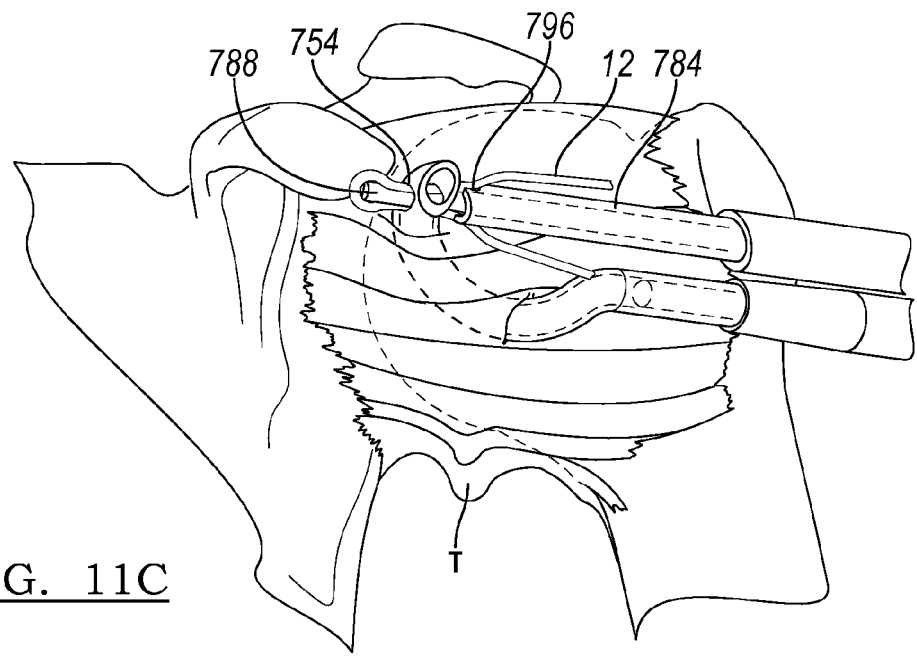
FIG. 11C is a perspective view of the suture passing instrument of FIG. 10 in an intermediate operative position depicting a pusher of the suture holder advanced through the needle tip.

Referring now to FIGS. 1A, 1B, and 11B, after the helical end 752 of the needle member 716 is fully inserted into the ligament, T, the actuator 22 is moved to the extended position. As previously described, the actuator 22 is fixedly attached to the slider mechanism 24, so that longitudinal movement of the actuator 22 to the extended position, in turn, causes movement of the slider mechanism 24. In particular, the actuator 22 drives the slider mechanism 24 towards the distal end 28 of the handle body 20. This longitudinal movement causes the first and second slide members 32, 36 to translate in the central cavity 30 and curved channels 34, respectively. The extending pin 114 of the second slide member 36 drivingly moves the short leg 118 of the c-shaped translation member 38. The concurrent movement of the first slide member 32 and the c-shaped translation member 38 cause the cannulated suture carrier 784 and the suture pusher 788 to extend through the tubular shaft 780 at an equivalent speed. Accordingly, the cannulated suture carrier 784 of the suture holder assembly 718 moves distally outwardly from the tubular shaft 780 directing the suture 12 towards the needle eyelet 754.

As the second slide member 36 reaches the distal end 28 of the handle body 20, the extending pin 114 curves away from the short leg 118, removing its longitudinal driving force. The c-shaped translation member 38 may then contact the stop 128 located at the distal end 28 of the handle body 20, preventing any further longitudinal movement of the c-shaped translation member 38 and the cannulated suture carrier 784. This stopped motion of the c-shaped translation member 38 equates to a stopped motion of the cannulated suture carrier 784 a predetermined distance from the eyelet 754 of the needle member 716.

With reference now to FIGS. 1A, 1B, 10, and 11C, the first slide member 32 continues its longitudinal translation through the central cavity 30, compressing the spring 40 as it moves. As should be understood, the suture pusher 788 continues movement with the first slide member 32, which causes its extension from the cannulated suture carrier 784. In this motion, the suture pusher 788 forces the suture 12 out of the channels 796. At least a portion of the suture pusher 788 extends through the needle eyelet 754, pushing the suture 12 into the eyelet 754.

Figure 11D:
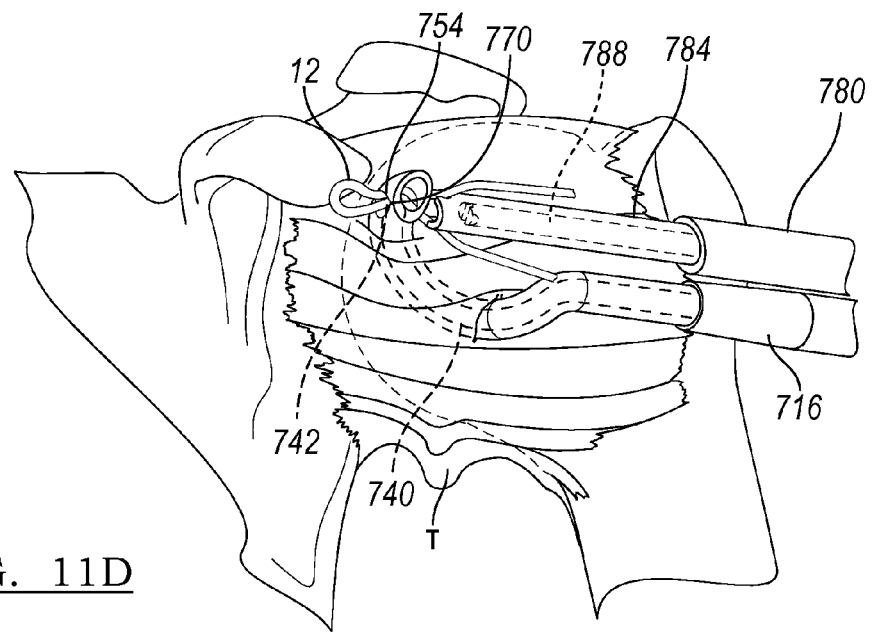
FIG. 11D is a perspective view of the suture passing instrument of FIG. 10 in an intermediate operative position depicting a lock rod advanced toward the needle tip.

Referring now to FIGS. 1A, 1B, and 11D, after the suture 12 extends through the needle eyelet 754 a predetermined distance, the operator may remove the longitudinal force from the actuator 22 allowing the first slide member 32 to snap back from the distal end 28 of the handle body 20 due to force from the spring 40. The lock rod 740 may then be advanced through the cannulated needle member 716 to pinch the suture 12 against the circular profile 770 with the blunt end 742, by advancing a second actuator (shown in phantom in FIG. 6 as member 44). The operator may then return the actuator 22 to the retracted position. Alternately, the lock rod 740 may be advanced and retracted in a single actuation motion (e.g., as a continuous motion from the actuator 22 as shown and described with respect to the operation handle and slider mechanism of copending U.S. Ser. No. 13/114,483 filed concurrently herewith; U.S. Provisional Application No. 61/348,016, filed on May 25, 2010) the disclosure of which is incorporated by reference herein in its entirety).

During retraction, the suture pusher 788 returns to its initial position within the cannulated suture carrier 784 and the cannulated suture carrier 784 is captured by the tubular shaft 780, as previously described with respect to the suture carrier 684. Notably, however, the suture 12 remains within the needle eyelet 754, retained by the blunt end 742 of the lock rod 740.

Figure 11E:
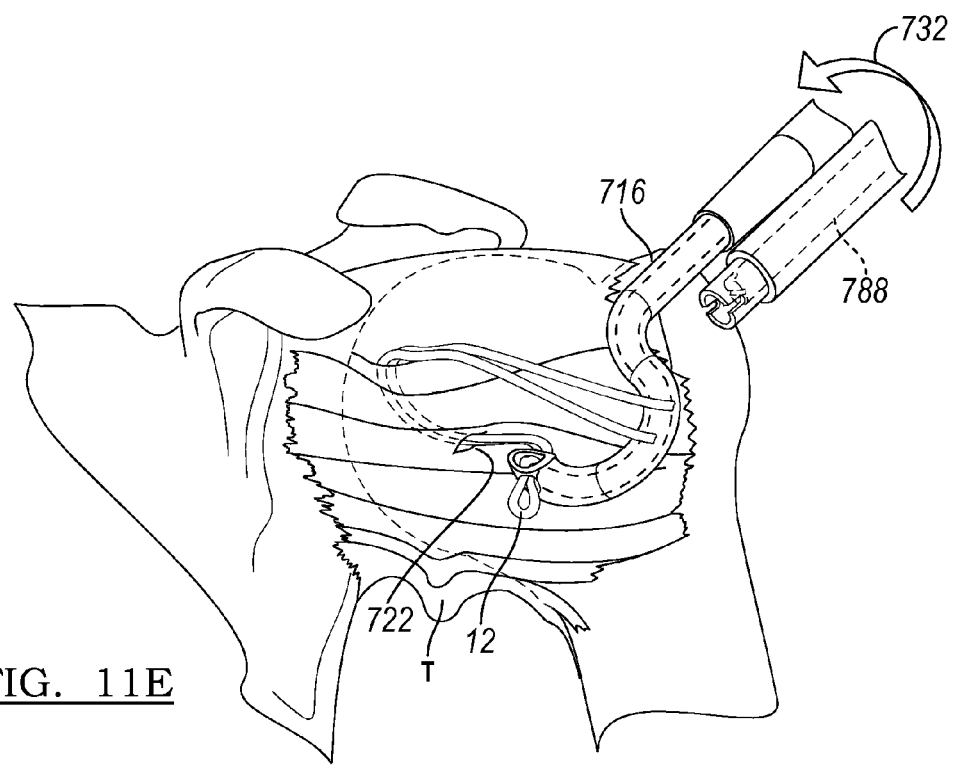
FIG. 11E is a perspective view of the suture passing instrument of FIG. 10 in a final retracted position in association with the glenohumeral tissue.

With reference now to FIGS. 1A, 1B, and 11E, the needle member 716 may then be withdrawn from the ligament, T, carrying the suture 12 therewith. Withdrawal of the needle member 716 is accomplished in reverse of insertion (i.e., rotation occurs in a clockwise motion), as shown by rotational arrow 732, with the needle member 716 being removed from the ligament, T, at the tissue opening 722. Ends of the suture 12 can then be knotted 134 outside of the surgical site, as previously shown in FIG. 4F.

Figure 12:
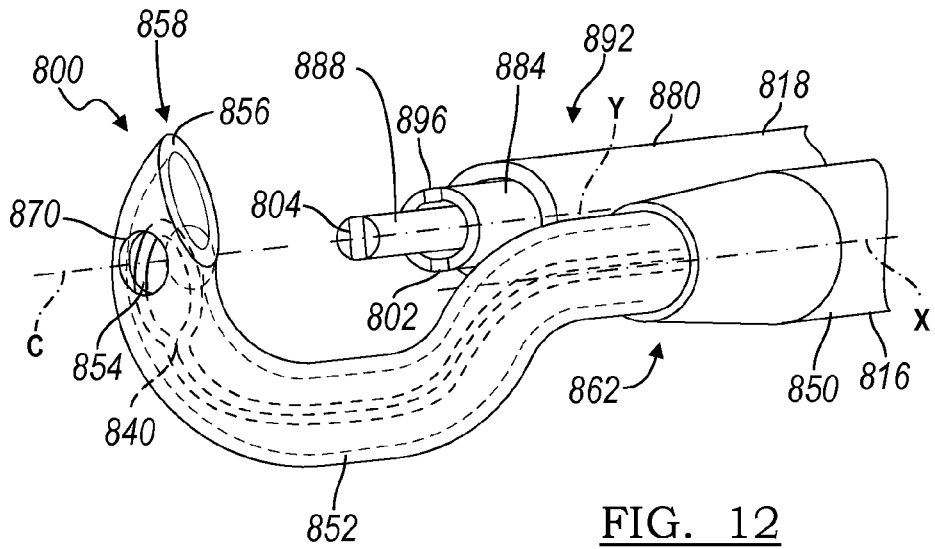
FIG. 12 is a perspective view of an alternate suture passing instrument constructed in accordance with the teachings of the present disclosure.

With reference now to FIG. 12, another alternative suture passing instrument 800 is shown. Suture passing instrument 800 is also operable for passing the suture 12 through the labrum 121 of the glenohumeral joint, T, to assist in repairing the tissue, as previously described with respect to suture passing instrument 10. Furthermore, suture passing instrument 800 uses a similar operation handle 14 and connection member 48, which are not shown and will not be described in detail herein. However, suture passing instrument 800 includes both an alternately designed cannulated needle member 816 and suture holder assembly 818 extending from the distal end 28 of the operation handle 14. Both the cannulated needle member 816 and suture holder assembly 818 may be fixedly coupled to the operation handle 14 and the connection member 48 to maintain a parallel relationship and to prevent relative movement therebetween.

The cannulated needle member 816 may include an elongated shaft 850, a tubular helical end 852 secured to the elongated shaft 850, a generally circular needle eyelet 854 extending through the helical end 852, a pointed tip 856 at a distal end 858 of the helical end 852, and a wire loop 840 extending through the elongated shaft 850 to the helical end 852 and surrounding the circular needle eyelet 854. While this embodiment depicts the helical end 852 separable from the elongated shaft 850, it should be understood that the elongated shaft 850 and the helical end 852 may also be integrally formed as shown in the aforementioned embodiments.

The elongated shaft 850 may extend along a longitudinal axis, X, a predetermined distance from the operation handle 14. The helical end 852 may extend from a distal end 862 of the elongated shaft 850 and may exhibit a "pig-tail" shape or helix curve over its length. The helix curve may be rotated either in a right- or left-handed direction to bring a centerline, C, of the needle eyelet 854 into a coaxial arrangement with a longitudinal axis, Y, of the suture holder assembly 818.

The needle eyelet 854 may define a generally circular profile 870 extending through opposite sides of the tubular surface of the cannulated needle member 816 (see FIG. 12A). Furthermore, the wire loop 840 may be movable from a first, extended position to a second, retracted position, both within the helical end 852 surrounding the needle eyelet 854. The wire loop 840 may be a material (e.g., nitinol) that generally maintains its biased open loop shape in both the extended and retracted positions, as will be described in more detail below.

Suture holder assembly 818 may include a generally tubular shaft 880, a cannulated suture carrier 884 telescopically received within the tubular shaft 880, and a suture pusher 888 telescopically received within the cannulated suture carrier 884. The generally tubular shaft 880 extends along the longitudinal axis, Y, and has a distal end 892 terminating near the distal end 862 of the elongated shaft 850 of the needle member 816. Cannulated suture carrier 884 may define a pair of opposing, parallel channels 896 having a predetermined length extending into the cannulated suture carrier 884 and may have a width for receipt of sutures of various sizes. Accordingly, the parallel channels 896 may have sidewalls 802 that are angled or arranged in a decreasing step arrangement. The suture pusher 888 may define a generally cylindrical pusher body 804 sized to be received within the eyelet 854 of the needle member 816. While suture passing instrument 800 is shown to include suture holder assembly 818, it is also contemplated that the suture holder assembly 18 may be used with this embodiment. As should be understood, each embodiment may interchange the suture holder assembly 18 and the suture holder assembly 818.

Operation of the suture passing instrument 800 will now be described with reference to the glenohumeral ligament, T, shown in FIGS. 13A-13E and the slider mechanism 24 shown in FIGS. 1A and 1B. Initially with the actuator 22 in the retracted position, the appropriately sized suture 12 is loaded into the parallel channels 896 of the cannulated suture carrier 884 transversely to the longitudinal axis, Y.

Figure 13A:
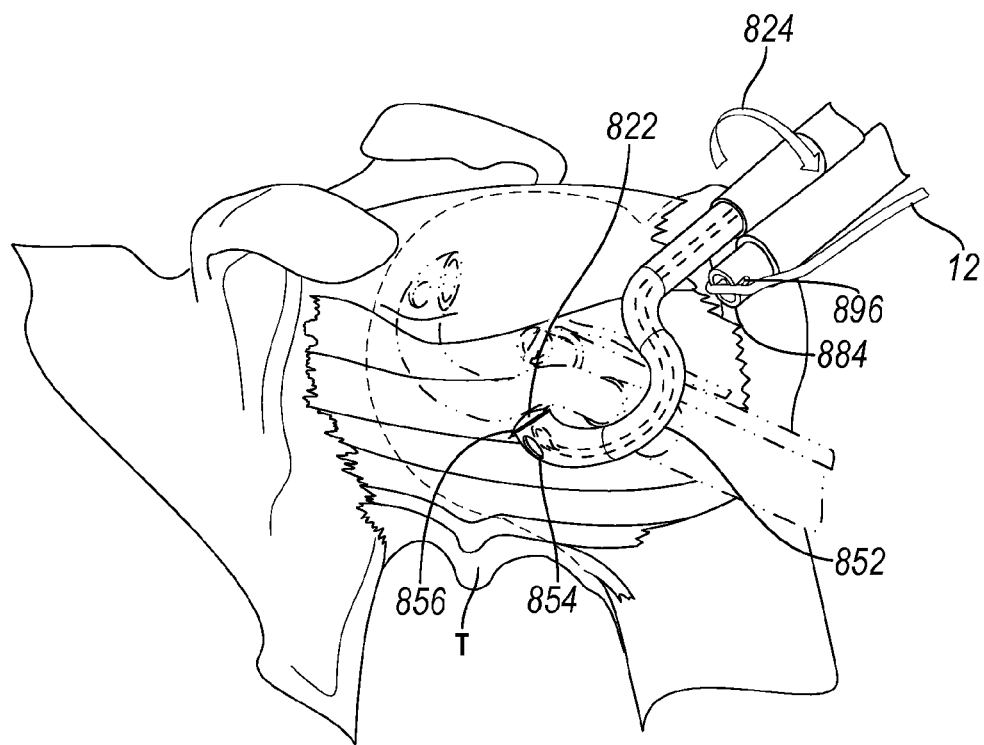
FIG. 13A is a perspective view of the suture passing instrument of FIG. 12 in an initial operative position in association with a glenohumeral tissue.

With particular reference to FIG. 13A, the pointed tip 856 of the helical end 852 is brought into contact with the labrum 121 (FIG. 4A) of the glenohumeral joint, T, with no rotational movement. The sharpened point of the tip 856 pierces the ligament, T, and allows the suture passing instrument 800 to establish an opening 822 within the ligament, T. As the suture passing instrument 800 is inserted through the opening 822, the operation handle 14 is rotated in a counter-clockwise manner, as shown by rotational arrow 824, in order to maintain a minimal size for the opening 822, as previously described. The operation handle 14 may be rotated anywhere between approximately one-quarter of a turn to one full revolution to extend the needle eyelet 854 out of the ligament, T. The amount of rotation for the operation handle 14 may depend upon the dimensional shape of the curve of the helical end 852. The final orientation of the helical end 852 is shown in phantom.

Figure 13B:
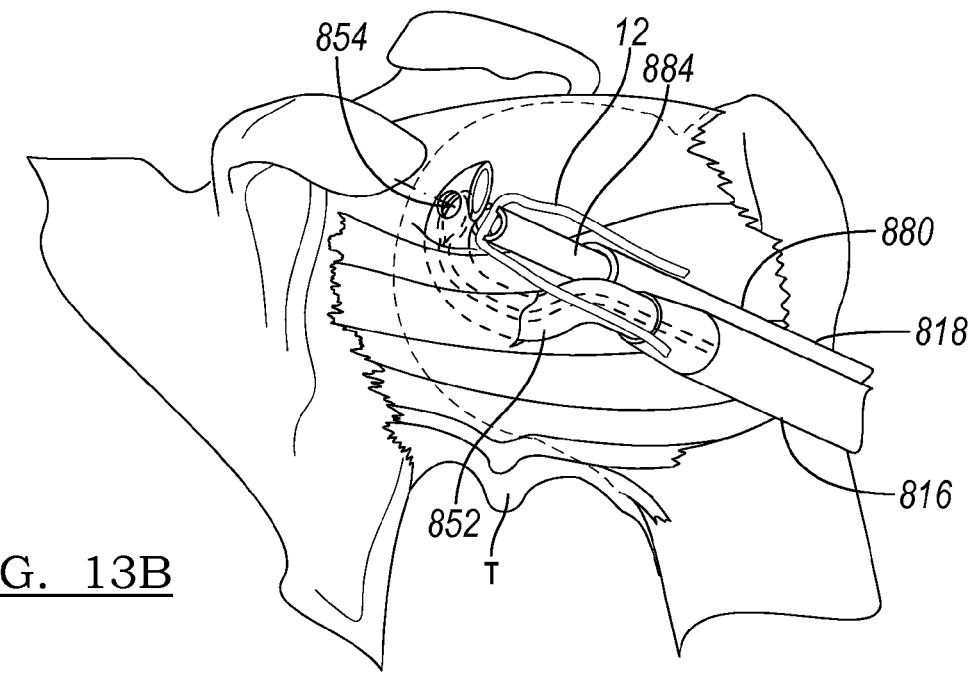
FIG. 13B is a perspective view of the suture passing instrument of FIG. 12 in an intermediate operative position depicting a suture holder advanced toward a needle tip.
Figure 13C:
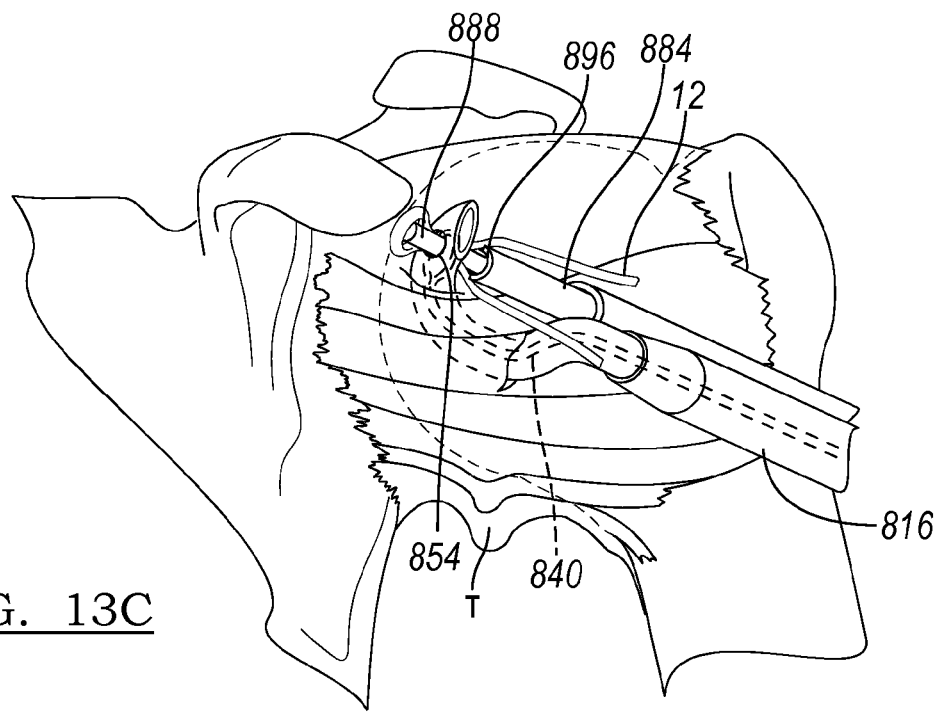
FIG. 13C is a perspective view of the suture passing instrument of FIG. 12 in an intermediate operative position depicting a pusher of the suture holder advanced through the needle tip.

Referring now to FIGS. 1A, 1B, and 13B, after the helical end 852 of the needle member 816 is fully inserted into the ligament, T, the actuator 22 is moved to the extended position. As previously described, the actuator 22 is fixedly attached to the slider mechanism 24, so that longitudinal movement of the actuator 22 to the extended position, in turn, causes movement of the slider mechanism 24. In particular, the actuator 22 drives the slider mechanism 24 towards the distal end 28 of the handle body 20. This longitudinal movement causes the first and second slide members 32, 36 to translate in the central cavity 30 and curved channels 34, respectively. The extending pin 114 of the second slide member 36 drivingly moves the short leg 118 of the c-shaped translation member 38. The concurrent movement of the first slide member 32 and the c-shaped translation member 38 cause the cannulated suture carrier 884 and the suture pusher 888 to extend through the tubular shaft 880 at an equivalent speed. Accordingly, the cannulated suture carrier 884 of the suture holder assembly 818 moves distally outwardly from the tubular shaft 880 directing the suture 12 towards the needle eyelet 854.

As the second slide member 36 reaches the distal end 28 of the handle body 20, the extending pin 114 curves away from the short leg 118, removing its longitudinal driving force. The c-shaped translation member 38 may then contact the stop 128 located at the distal end 28 of the handle body 20, preventing any further longitudinal movement of the c-shaped translation member 38 and the cannulated suture carrier 884. This stopped motion of the c-shaped translation member 38 equates to a stopped motion of the cannulated suture carrier 884 a predetermined distance from the eyelet 854 of the needle member 816.

With reference now to FIGS. 1A, 1B, 12, and 13C, the first slide member 32 continues its longitudinal translation through the central cavity 30, compressing the spring 40 as it moves. As should be understood, the suture pusher 888 continues movement with the first slide member 32, which causes its extension from the cannulated suture carrier 884. In this motion, the suture pusher 888 forces the suture 12 out of the channels 896. At least a portion of the suture pusher 888 extends through the needle eyelet 854, pushing the suture 12 into the eyelet 854.

Figure 13D:
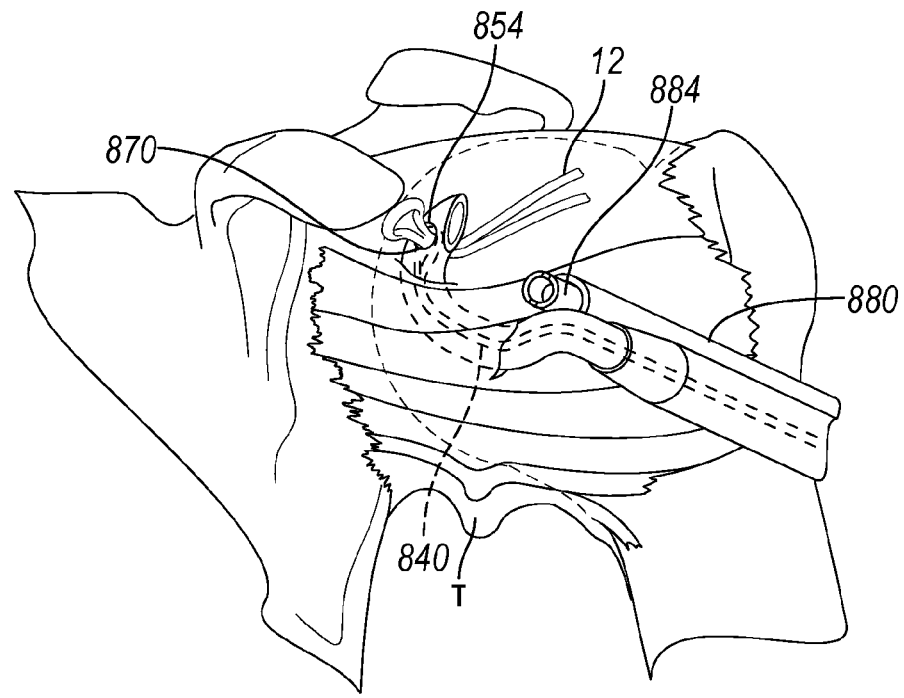
FIG. 13D is a perspective view of the suture passing instrument of FIG. 12 in an intermediate operative position depicting a wire loop retracted from the needle tip.

Referring now to FIGS. 1A, 1B, and 13D, after the suture 12 extends through the needle eyelet 854 a predetermined distance, the operator may remove the longitudinal force from the actuator 22 allowing the first slide member 32 to snap back from the distal end 28 of the handle body 20 due to force from the spring 40. The wire loop 840 may then be retracted within the cannulated needle member 816 to pinch the suture 12 against the circular profile 870 of the eyelet 854, by advancing a second actuator (shown in phantom in FIG. 6 as member 44). The operator may then return the actuator 22 to the retracted position. Alternately, the wire loop 840 may be advanced and retracted in a single actuation motion (e.g., as a continuous motion from the actuator 22 as previously described with respect to lock rod 740.

During retraction, the suture pusher 888 returns to its initial position within the cannulated suture carrier 884 and the cannulated suture carrier 884 is captured by the tubular shaft 880, as previously described with respect to the suture carrier 684. Notably, however, the suture 12 remains within the needle eyelet 854, pinched against the needle eyelet 854 with the wire loop 840.

Figure 13E:
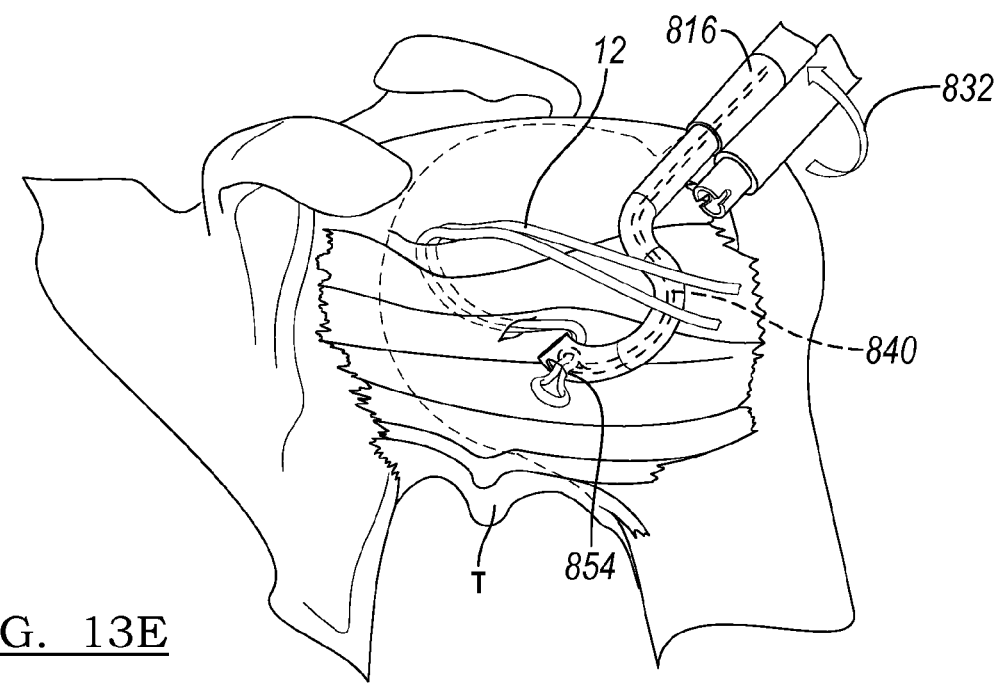
FIG. 13E is a perspective view of the suture passing instrument of FIG. 12 being removed from the glenohumeral tissue.

With reference now to FIGS. 1A, 1B, and 13E, the needle member 816 may then be withdrawn from the ligament, T, carrying the suture 12 therewith. Withdrawal of the needle member 816 is accomplished in reverse of insertion (i.e., rotation occurs in a clockwise motion), as shown by rotational arrow 832, with the needle member 816 being removed from the ligament, T, at the tissue opening 822. Ends of the suture 12 can then be knotted 134 outside of the surgical site, as previously shown in FIG. 4F.

Figure 14A:
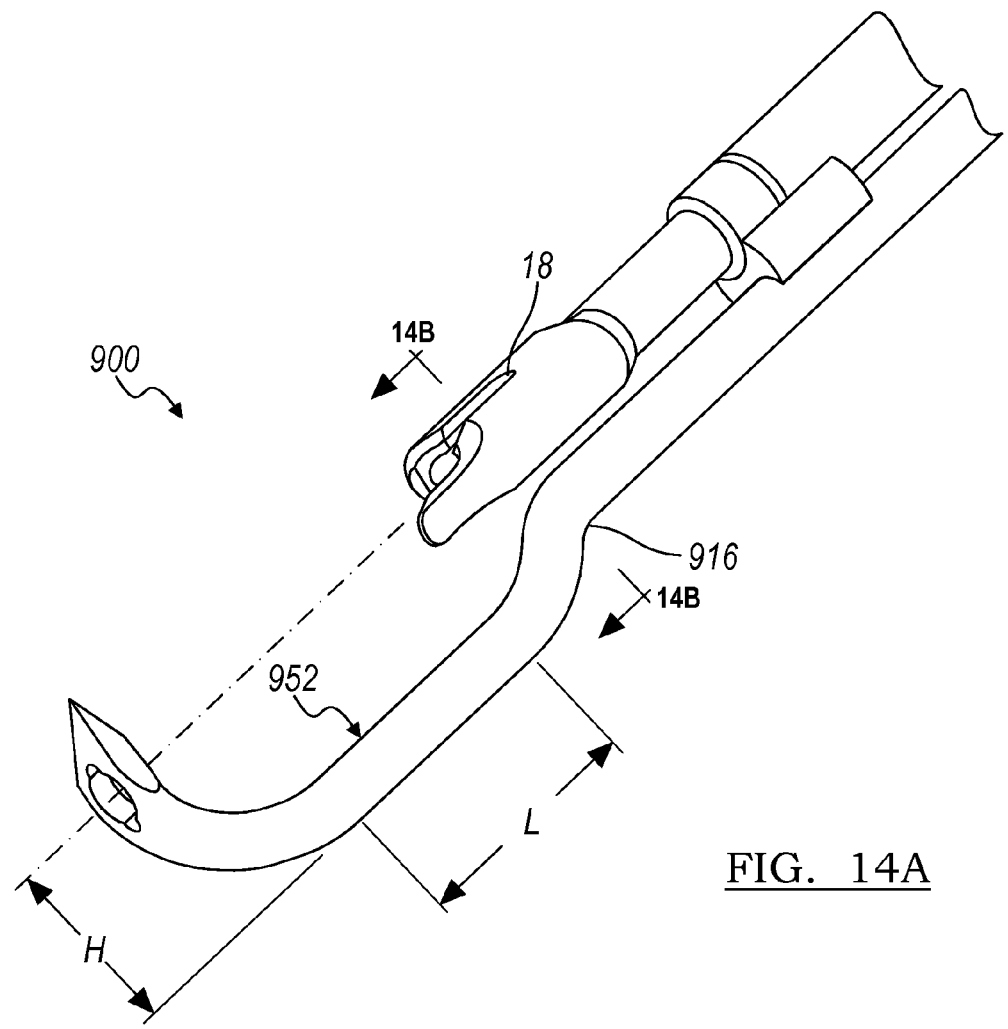
FIG. 14A is a perspective view of an alternate suture passing instrument constructed in accordance with the teachings of the present disclosure.
Figure 14B:
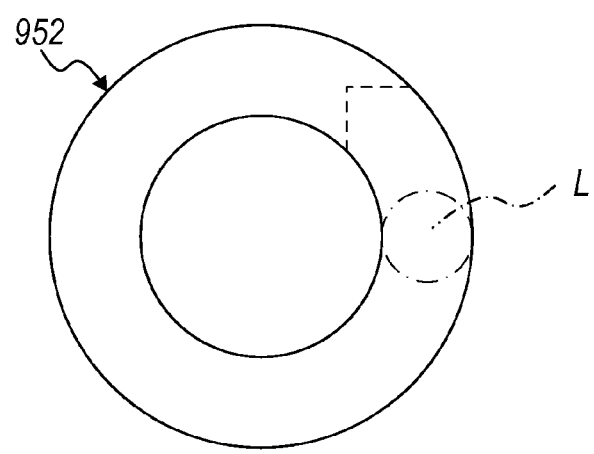
FIG. 14B is an end view of the alternate suture passing instrument of FIG. 14A.

Referring now to FIGS. 14A and 14B, another alternative suture passing instrument 900 is shown. Suture passing instrument 900 is also operable for passing the suture 12 through the labrum 121 to assist in repairing the joint, as previously described with respect to suture passing instrument 10. Furthermore, many of the components of the suture passing instrument 10 remain unchanged in suture passing instrument 900. For example, suture passing instrument 900 uses a similar operation handle 14 and suture holder assembly 18. Suture passing instrument 900, however, exhibits an elongated helix curve at a helical end 952 of a needle member 916, rather than the helix curve described with respect to the suture passing instrument 10. In particular, the elongated helix curve may follow a constant radius rotated about a central axis of the needle member 916, stop rotation and extend along a straight length, L, then continue following the constant radius rotated about the central axis of the needle member 916. Both the suture passing instrument 10 and the suture passing instrument 900 will exhibit a similar end view as shown in FIG. 14B (elongated straight length, L, shown in phantom).

Accordingly, during insertion of the suture passing instrument 900, the operation handle 14 must be extended before being rotated in a clockwise manner in order to maintain the minimal size for the opening 122. The suture passing instrument 900 defines an elongated section, L, which may be at least as large as a height section, H. The elongated section, L, and the height section, H, form a trough which is substantially longer than the trough created by the helix of suture passing instrument 10. Such an arrangement allows more tissue to be captured by the suture passing instrument 900 without increasing the size of the cannulated needle member 916 as compared to a traditional helix shape. While suture passing instrument 10 and suture passing instrument 900 are highly similar, certain surgeons may prefer one design to the other due to the amount of tissue needing to be secured.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure. For example, while the connection member 48 is shown and described for maintaining a parallel relationship between the needle members and suture holder assemblies, these members may be immovably secured in any other way known in the art, including but not limited to soldering, gluing, integrally forming, etc. Furthermore, in certain embodiments it may not be necessary to immovably secure the needle members and suture holder assemblies by any means.

What is claimed is:

1. A suture passing instrument comprising:
an operation handle having at least one actuator movable between a first position and a second position and a slider mechanism operable by the actuator and including first and second pivotally attached slide members, the first slide member movable longitudinally along and inside a central cavity formed inside the handle body and the second slide member movable longitudinally along and inside a curved channel formed inside the handle body;
a needle member extending from the operation handle, the needle member having a curved end portion with a distal end and defining an eyelet extending therethrough at the distal end of the curved end portion wherein the needle member is cannulated and includes an interference member movable within the needle member to lock the suture within the eyelet; and
a suture holder assembly extending from the operation handle and being external to the needle member, the suture holder assembly has a movable suture carrier at a distal end configured to hold a suture, the movable suture carrier having a suture pusher telescopically and movably received in the movable suture carrier, wherein the suture carrier is movable between a retracted position and an extended position, wherein the suture pusher is movable beyond the suture carrier to carry the suture from outside the needle member and through the eyelet transversely to the distal end of the needle member.

2. The suture passing instrument of claim 1, wherein the curved end portion is one of a right helix curve, a left helix curve, and a linear curve.

3. The suture passing instrument of claim 2, wherein the curved end portion further comprises an elongated portion.

4. The suture passing instrument of claim 1, wherein a centerline of the eyelet is coaxially aligned with a longitudinal axis of the suture holder assembly.

5. The suture passing instrument of claim 1, wherein the eyelet has a hexagonal periphery defining an eyelet opening.

6. The suture passing instrument of claim 5, wherein a pair of semi-circular openings are arranged at distal and proximal ends of the hexagonal periphery.

7. The suture passing instrument of claim 1, wherein the suture carrier defines a pair of opposed channels extending inwardly from an end face thereof, the channels configured to receive the suture therein.

8. The suture passing instrument of claim 7, wherein the channels have one of angled sidewalls, straight sidewalls, or stepped sidewalls.

9. The suture passing instrument of claim 7, wherein the suture carrier defines a nose portion extending outwardly from the end face of the suture carrier, the nose portion angled to direct the suture into the opposed channels.

10. The suture passing instrument of claim 1, wherein the interference member is one of a movable lock rod or a wire loop.

11. The suture passing instrument of claim 1, further comprising an opening extending from the eyelet defining a pair of opposing faces, the opposing faces extending from the eyelet to a distal tip of the needle member, the eyelet expandable from a first diameter to a second diameter by biasing the opposing faces apart using the suture pusher.

12. The suture passing instrument of claim 1, wherein the needle member and the suture holder assembly are substantially parallel over their lengths.

13. The suture passing instrument of claim 1, wherein the curved end portion of the needle member is removable.

14. The suture passing instrument of claim 1, wherein the suture pusher defines a cylindrical body reducing in size to a pair of parallel surfaces and a hook member at a pusher end face.

15. A suture passing instrument comprising:
an operation handle having an actuator movable between a first position and a second position;
a cannulated needle member having an internal bore and extending from the operation handle, the needle member having a straight portion along a first longitudinal axis, a curved end portion extending from the straight portion and defining an eyelet extending therethrough at the distal end of the curved end portion; and
a suture holder assembly extending from the operation handle, the suture holder assembly has a movable suture carrier at a distal end configured to hold a suture, the movable suture carrier having a suture pusher telescopically and movably received in the movable suture carrier along a second longitudinal axis parallel to the first longitudinal axis and outside the bore of the needle member, wherein the suture carrier is movable between a retracted position and an extended position, wherein the suture pusher is movable beyond the suture carrier to carry the suture through the eyelet of the needle member; and
a flexible longitudinal interference member received within the internal bore of the cannulated needle member and movable from a retracted position in the straight portion to an extended position in the curved end portion to lock the suture within the eyelet of the needle member.

16. The suture passing instrument of claim 15, wherein the interference member is one of a movable lock rod or a wire loop.

17. The suture passing instrument of claim 15, wherein the operation handle includes a handle body receiving the actuator and a slider mechanism disposed therein and operable by the actuator.

18. The suture passing instrument of claim 17, wherein the slider mechanism includes first and second pivotally attached slide members, a c-shaped translation member and a spring.

19. The suture passing instrument of claim 18, wherein the first slide member is movable longitudinally along a central cavity of the handle body.

20. The suture passing instrument of claim 19, wherein the second slide member is movable longitudinally along one of first and second curved channels formed inside the handle body mirrored about a center axis of the handle for left and right-handed operation.

21. A suture passing instrument comprising:
an operation handle having a handle body, an actuator received in the handle body and movable between a first position and a second position and a slider mechanism operable by the actuator and including first and second pivotally attached slide members, the first slide member movable longitudinally along and inside a central cavity formed inside the handle body and the second slide member movable longitudinally along and inside a curved channel formed inside the handle body;
a cannulated needle member having an internal bore and extending from the operation handle, the needle member having a straight portion along a first longitudinal axis, a curved end portion extending from the straight portion and defining an eyelet extending therethrough at the distal end of the curved end portion;
a suture holder assembly extending from the operation handle, the suture holder assembly has a movable suture carrier at a distal end configured to hold a suture, the movable suture carrier having a suture pusher telescopically and movably received in the movable suture carrier along a second longitudinal axis parallel to the first longitudinal axis and outside the bore of the needle member, wherein the suture carrier is movable between a retracted position and an extended position, wherein the suture pusher is movable beyond the suture carrier to carry the suture through the eyelet of the needle member; and an interference member movable within the cannulated needle member to retain the suture within the eyelet.

22. The suture passing instrument of claim 21, wherein the slider mechanism further comprises a c-shaped translation member and a spring.

23. The suture passing instrument of claim 21, wherein the curved channel is one of first and second curved channels mirrored about a central axis for left and right-handed operation.

* * * * *

UNITED STATES PATENT AND TRADEMARK OFFICE
CERTIFICATE OF CORRECTION

PATENT NO. : 8,709,022 B2  
APPLICATION NO. : 13/114488  
DATED : April 29, 2014  
INVENTOR(S) : Kevin T. Stone et al.

Page 1 of 2

It is certified that error appears in the above-identified patent and that said Letters Patent is hereby corrected as shown below:

In the Specification

Column 6, Line 23; Delete "nose" and insert --extended nose--.
Column 6, Line 27; Delete "nose" and insert --extended nose--.
Column 6, Line 35; Delete "eyelet" and insert --needle eyelet--.
Column 6, Line 39; Delete "eyelet" and insert --needle eyelet--.
Column 6, Line 43; Delete "eyelet" and insert --needle eyelet--.
Column 7, Line 1; Delete "channel" and insert --curved channel--.
Column 7, Line 16; Delete "nose" and insert --extended nose--.
Column 7, Line 60; Delete "channel" and insert --curved channel--.
Column 7, Line 67; Delete "nose" and insert --extended nose--.
Column 9, Line 52; Delete "nose" and insert --extending nose--.
Column 10, Line 56; Delete "eyelet" and insert --needle eyelet--.
Column 11, Line 50; Delete "eyelet" and insert --needle eyelet--.
Column 11, Line 64; Delete "eyelet" and insert --needle eyelet--.
Column 13, Line 11; After "distal", insert --end of--.
Column 13, Line 29; Delete "eyelet" and insert --needle eyelet--.
Column 14, Line 22; Delete "eyelet" and insert --needle eyelet--.
Column 14, Line 33; Delete "eyelet" and insert --needle eyelet--.
Column 14, Line 49; Delete "herewith; U.S." and insert --herewith (U.S.--.
Column 14, Line 55; Delete "suture" and insert --cannulated suture--.
Column 15, Line 59; Delete "eyelet" and insert --needle eyelet--.
Column 16, Line 52; Delete "eyelet" and insert --needle eyelet--.
Column 16, Line 63; Delete "eyelet" and insert --needle eyelet--.
Column 17, Line 4; Delete "eyelet" and insert --needle eyelet--.
Column 17, Line 10; Delete "740." and insert --740).--.
Column 17, Line 14; Delete "suture" and insert --cannulated suture--.

Signed and Sealed this  
Twenty-seventh Day of January, 2015

Michelle K. Lee  
*Deputy Director of the United States Patent and Trademark Office*

CERTIFICATE OF CORRECTION (continued)
U.S. Pat. No. 8,709,022 B2

In the Claims

Column 19, Line 27, Claim 15; after "portion;" delete "and".